US012799456B2

(12) United States Patent
Henry et al.

(10) Patent No.: US 12,799,456 B2
(45) Date of Patent: Nov. 17, 2026

(54) GALECTIN-9 SPECIFIC BINDING AGENTS FOR USE IN TREATING CANCER

(71) Applicants: Emory University, Atlanta, GA (US); Children's Healthcare of Atlanta, Inc., Atlanta, GA (US)

(72) Inventors: Curtis J. Henry, Atlanta, GA (US); Jamie A. G. Hamilton, Atlanta, GA (US); Sunil S. Raikar, Decatur, GA (US); Anthony Ross, Atlanta, GA (US); Miyoung Lee, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 805 days.

(21) Appl. No.: 18/017,470

(22) PCT Filed: Jul. 23, 2021

(86) PCT No.: PCT/US2021/043017

§ 371 (c)(1),
(2) Date: Jan. 23, 2023

(87) PCT Pub. No.: WO2022/020745

PCT Pub. Date: Jan. 27, 2022

(65) Prior Publication Data

US 2023/0295564 A1 Sep. 21, 2023

Related U.S. Application Data

(60) Provisional application No. 63/055,662, filed on Jul. 23, 2020.

(51) Int. Cl.

| | |
|---|---|
| ***C12N 5/0783*** | (2010.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 14/725*** | (2006.01) |
| ***C07K 16/28*** | (2006.01) |
| ***C12N 15/85*** | (2006.01) |

(52) U.S. Cl.

CPC ............ *C12N 5/0636* (2013.01); *A61K 40/11* (2025.01); *A61K 40/31* (2025.01); *A61K 40/4256* (2025.01); *A61P 35/00* (2018.01); *C07K 14/7051* (2013.01); *C07K 14/70521* (2013.01); *C07K 16/2851* (2013.01); *C12N 15/85* (2013.01)

(58) Field of Classification Search

None

See application file for complete search history.

(56) References Cited

U.S. PATENT DOCUMENTS

| | | | |
|---|---|---|---|
| 10,344,091 | B2 | 7/2019 | Koide |
| 2017/0037133 | A1 | 2/2017 | Fiedler |
| 2017/0283499 | A1 | 10/2017 | Delhem |
| 2019/0077869 | A1 | 3/2019 | Fiedler |
| 2019/0127474 | A1 | 5/2019 | Wykes |

OTHER PUBLICATIONS

Williams, et al. (2006) "Arf gene loss enhances oncogenicity and limits imatinib response in mouse models of Bcr-Abl-induced acute lymphoblastic leukemia", Proceedings of the National Academy of Sciences, USA, 103(17): 6688-96. (Year: 2006).*

Castellarin, et al. (2020) "A rational mouse model to detect on-target, off-tumor CAR T cell toxicity", JCI Insight, 5(14): article e136012, 16 pages long. (Year: 2020).*

Bi, et al. (2011) "Galectin-9 binding to cell surface protein disulfide isomerase regulates the redox environment to enhance T-cell migration and HIV entry", Proceedings of the National Academy of Sciences, USA., (108)26: 10650-55. (Year: 2011).*

Lee, et al. (2022) "Obesity-induced galectin-9 is a therapeutic target in B-cell acute lymphoblastic leukiemia", Nature Communications, 13: 1157, 16 pages. (Year: 2022).*

Wong, et al. (2019) "Comparative Analysis of the CDR Loops of Antigen Receptors", Frontiers in Immunology, 10: Article 2454, 11 pages long. (Year: 2019).*

Ayres, et al. (2016) "Differential utilization of binding loop flexibility in T cell receptor ligand selection and cross-reactivity", Scientific Reports (Nature), 6: Article 25070, 14 pages long. (Year: 2016).*

Behan et al. Adipocytes impair leukemia treatment in mice, Cancer Res. 2009, 69(19): 7867-7874.

Biolegend (TM) Purified anti-human Galectin-9 Antibody, 2022.

Fujita et al. Cancer Therapy Due to Apoptosis: Galectin-9, Int. J. Mol. Sci. 2017, 18, 74.

Giovannone et al. Galectin-9 suppresses B cell receptor signaling and is regulated by I-branching of N-glycans, Nature Communications, 2018, 9:3287.

June et al. Chimeric Antigen Receptor Therapy, N Engl J Med, 2018, 379:64-73.

Lee et al. Combinatorial Inhibition of Galectin-9 and CHK1 Represent a Novel Treatment Strategy for T-Cell Acute Lymphoblastic Leukemia, Blood 138 (2021) 4400-4401.

(Continued)

*Primary Examiner* — Robert M Kelly

(74) *Attorney, Agent, or Firm* — Emory Patent Group

(57) ABSTRACT

This disclosure relates to uses of galectin-9 specific binding agents and chimeric antigen receptors in methods of treating cancer such as hematological cancers or solid tumors. In certain embodiments, the galectin-9 specific binding agent is a TIM3, CD44, CD40, CLEC7a (Dectin-1), or CD137 (4-IBB) extracellular domain, an anti-galectin-9) antibody, specific binding single chain antibody, fragment, or variant thereof. In certain embodiments, cancer treatment is a cell-based therapy using chimeric antigen receptors having a galectin-9 targeting sequence.

2 Claims, 5 Drawing Sheets

Specification includes a Sequence Listing.

(56) References Cited

OTHER PUBLICATIONS

Lee et al. Obesity-induced galectin-9 is a therapeutic target in B-cell acute lymphoblastic leukemia, Nature Communications, 2022, 13:1157.
Orgel et al. Obesity is associated with residual leukemia following induction therapy for childhood B-precursor acute lymphoblastic leukemia, Blood. 2014, 124(26):3932-3938.
Pena et al. Galectins as therapeutic targets for hematological malignancies: a hopeful sweetness, Ann Transl Med 2014, 2(9):87.
Ruvolo et al. Galectins as regulators of cell survival in the leukemia niche, Advances in Biological Regulation 71 (2019) 41-54.
Silva et al. The Tim-3-galectin-9 Secretory Pathway is Involved in the Immune Escape of Human Acute Myeloid Leukemia Cells, EBioMedicine 22 (2017) 44-57.
Ye et al. Leukemic stem cells evade chemotherapy by metabolic adaptation to an adipose tissue niche, Cell Stem Cell. 2016, 19(1): 23-37.

* cited by examiner

GALECTIN-9 SPECIFIC BINDING AGENTS FOR USE IN TREATING CANCER

CROSS-REFERENCE TO RELATED APPLICATIONS

This application is the National Stage of International Application No. PCT/US2021/043017 filed Jul. 23, 2021, which claims the benefit of U.S. Provisional Application No. 63/055,662 filed Jul. 23, 2020. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18091_ST25.txt. The text file is 29 KB, was created on Jul. 22, 2021, and is being submitted electronically via EFS-Web.

BACKGROUND

Leukemia is cancer of the bone marrow and the lymphatic system that usually results in the production of leukemia cells. As the number of leukemia cells increases normal white blood cells, red blood cells, and platelets are reduced. Treating leukemia can be complex, lasts several years, and is not universally effect. For example, children with leukemia often receive a standard three drug therapy of L-asparaginase, vincristine, and dexamethasone for the first month of treatment. For children in high-risk groups, a fourth drug such as daunorubicin may be added. This treatment is followed by treatment with other chemotherapy agents such as methotrexate and 6-mercaptopurine. Some of the agents are administered into the cerebrospinal fluid (CSF) in order to target and prevent leukemia cells from spreading to the brain and spinal cord. There is a need for improved therapeutic options.

June et al. report on the use of vectors that encode CD19 targeted chimeric antigen receptors for the treatment of B-cell leukemias and lymphomas. N Engl J Med, 2018, 379:64-73. Behan et al. report adipocytes impair leukemia treatment in mice. Cancer Res. 2009, 69(19): 7867-7874. Ye et al., report leukemic stem cells evade chemotherapy by metabolic adaptation to an adipose tissue niche. Cell Stem Cell, 2016. 19(1):23-37.

Lectins are polysaccharide-binding proteins ubiquitous in nature having numerous roles in biological processes. Galectins are lectins that bind specifically to β-galactoside sugars. Fujita et al. report that galectin-9 is a candidate anti-cancer agent based on the carbohydrate recognition function. Int J Mol Sci, 2017, 18(1): 74. Silva et al. report the TIM-3-galectin-9 secretory pathway is involved in the immune escape of human acute myeloid leukemia cells. EBioMedicine, 2017, 22:44-57. Delham et al. report an antibody which is directed against galectin-9 and its use as an inhibitor of the suppressor activity of regulatory T lymphocytes. US Pub. Pat. App. No. 2017/0283499.

References cited herein are not an admission of prior art.

SUMMARY

This disclosure relates to uses of galectin-9 specific binding agents and chimeric antigen receptors in methods of treating cancer such as hematological cancers or solid tumors. In certain embodiments, the galectin-9 specific binding agent is a TIM3, CD44, CD40, CLEC7a (Dectin-1), or CD137 (4-1BB) extracellular domain, an anti-galectin-9 antibody, specific binding single chain antibody, fragment, or variant thereof. In certain embodiments, cancer treatment is a cell-based therapy using chimeric antigen receptors having a galectin-9 targeting sequence.

In certain embodiments, the subject is overweight or obese, e.g., diagnosed with a body mass index of 25, 30, 35 or greater. In certain embodiments, the subject is less than 5, 10, or 20 years old. In certain embodiments, the subject is more than 50, 55, or 60 years old.

In certain embodiments, cancer treatment methods comprise administering an effective amount of a galectin-9 specific binding agent or immune effector cell comprising a chimeric antigen receptor containing a galectin-9 specific binding agent to a subject in need thereof. In certain embodiments, this disclosure relates to methods of treating cancer comprising isolating immune effector cells, such as T cells, e.g., from a subject; transfecting the cells with a vector encoding a chimeric antigen receptor, wherein the chimeric antigen receptor encodes a galectin-9 specific binding agent; culturing the cells under conditions such that the chimeric antigen receptor comprising the galectin-9 specific binding agent is expressed on the surface of the cells providing galectin-9 targeted immune effector cells; and administering an effective of amount of the galectin-9 targeted immune effector cells to the subject.

In certain embodiments, the subject to be treated is diagnosed with cancer such as a metastatic or non-metastatic tumor or a hematological malignancy. Such malignancies include leukemias and lymphomas, such as acute lymphoblastic leukemia (ALL), B-cell acute lymphoblastic leukemia (B-ALL), acute myelogenous leukemia (AML), chronic lymphocytic leukemia (CLL), small lymphocytic lymphoma (SLL), chronic myelogenous leukemia (CML), acute monocytic leukemia (AMA) and/or other leukemias. In certain embodiments, the subject is diagnosed with a lymphoma such as all subtypes of Hodgkin's lymphoma or non-Hodgkin's lymphoma. In certain embodiments, the subject is diagnosed with a plasma cell malignancy such as multiple myeloma. In certain embodiments, the subject is diagnosed with breast cancer, prostate cancer, uterine cancer, ovarian cancer, lung cancer, skin cancer, stomach cancer, mouth cancer, esophageal cancer, kidney cancer (renal carcinoma), pancreatic cancer, liver cancer (hepatocellular carcinoma), gallbladder cancer, thyroid cancer, or brain cancer (neuroblastoma).

DETAILED DESCRIPTION

Figure 1:
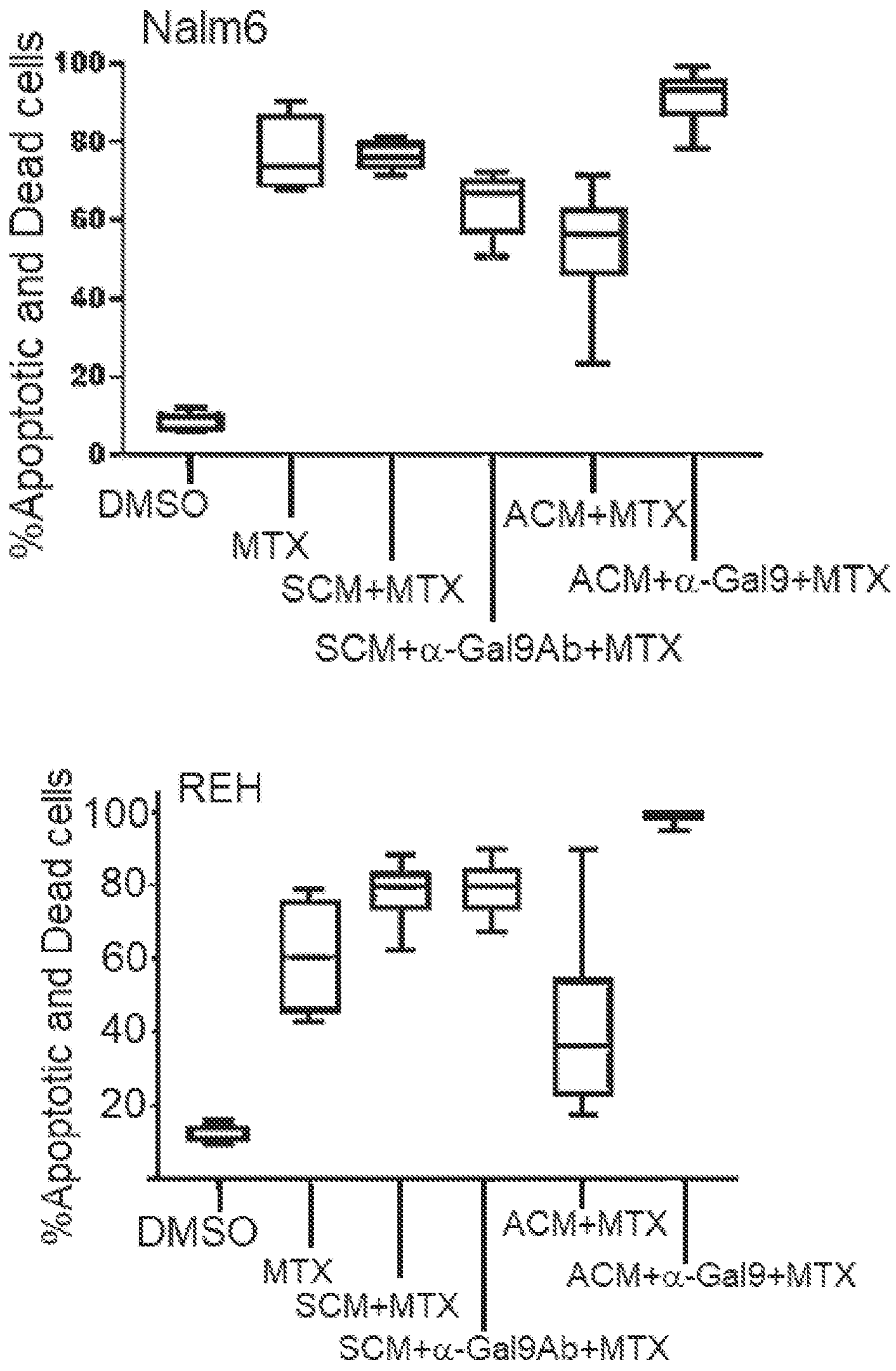
FIG. 1 shows data indicating treatment with anti-galectin-9 antibody alters cell cycle progression and induces cell death in human B-ALL cells in the presence of adipocyte-secreted factors. Human B-ALL cell lines (Nalm6, REH,) were cultured for 24 hours in unconditioned medium (RPMI), stromal cell-conditioned medium (SCM), or adipocyte-conditioned medium (ACM) and then treated with anti-GAL-9 antibody (αGAL-9 Ab) or an IgG control antibody (IgG ctrl) for an additional 2 days with or without MTX. The percentage of apoptotic and dead cells on day 3 of culture was determined using Annexin-V/PI staining followed by flow cytometric analysis.
Figure 2:
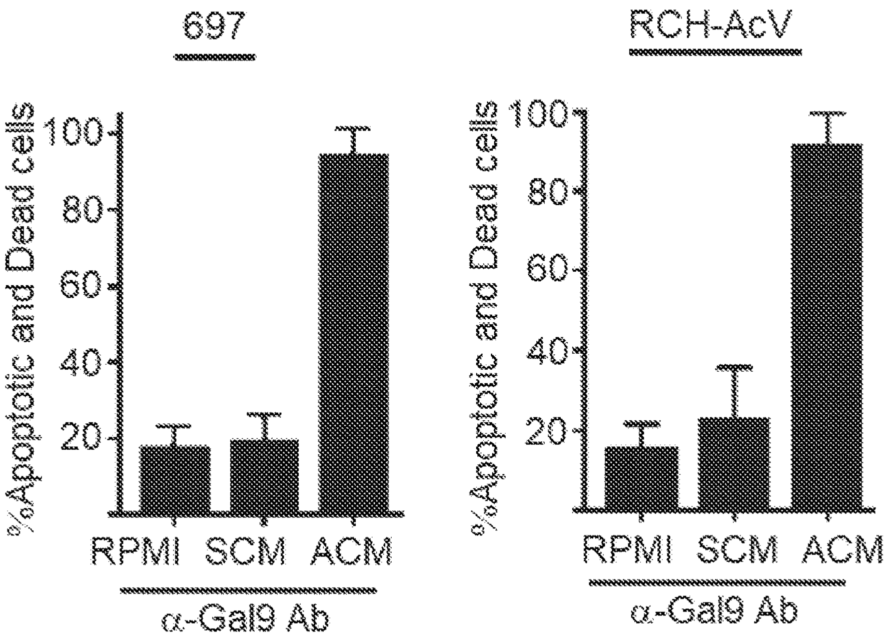
FIG. 2 shows data indicating treatment with anti-galectin-9 antibody alters cell cycle progression and induces cell death in human B-ALL cells line (697, and RCH-AcV).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms “a,” “an,” and “the” include plural referents unless the context clearly dictates otherwise. In this specification and in the claims that follow, reference will be made to a number of terms that shall be defined to have the following meanings unless a contrary intention is apparent.

As used in this disclosure and claim(s), the words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) have the meaning ascribed to them in U.S. Patent law in that they are inclusive or open-ended and do not exclude additional, unrecited elements or method steps.

“Consisting essentially of” or “consists of” or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods.

The term “comprising” in reference to a peptide having an amino acid sequence refers a peptide that may contain additional N-terminal (amine end) or C-terminal (carboxylic acid end) amino acids, i.e., the term is intended to include the amino acid sequence within a larger peptide. The term “consisting of” in reference to a peptide having an amino acid sequence refers a peptide having the exact number of amino acids in the sequence and not more or having not more than a rage of amino acids expressly specified in the claim. In certain embodiments, the disclosure contemplates that the “N-terminus of a peptide may consist of an amino acid sequence,” which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

"Subject" refers to any animal, preferably a human patient, livestock, rodent, monkey or domestic pet.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages, and mast cells; the lymphoid cell line produces B, T, NK, and plasma cells. Lymphomas, lymphocytic leukemias, and myeloma are from the lymphoid line, while acute and chronic myelogenous leukemia, myelodysplastic syndromes and myeloproliferative diseases are myeloid in origin.

A "chemotherapy agent," "chemotherapeutic," "anti-cancer agent," or the like, refer to molecules that are recognized to aid in the treatment of a cancer. Contemplated examples include the following molecules or derivatives such as abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

The term "effective amount" refers to that amount of a compound or pharmaceutical composition described herein that is sufficient to effect the intended application including, but not limited to, disease treatment, as illustrated below. In relation to a combination therapy, an "effective amount" indicates the combination of agent results in synergistic or additive effect when compared to the agents individually. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

The term "specific binding agent" refers to a molecule, such as a proteinaceous molecule, that binds a target molecule with a greater affinity than other random molecules or proteins. Examples of specific binding agents include antibodies that bind an epitope of an antigen. "Specifically binds" refers to the ability of a specific binding agent (such as an ligand, receptor, enzyme, antibody or binding region/fragment thereof) to recognize and bind a target molecule or polypeptide, such that its affinity (as determined by, e.g., affinity ELISA or other assays) is at least 10 times as great, but optionally 50 times as great, 100, 250 or 500 times as great, or even at least 1000 times as great as the affinity of the same for any other or other random molecule or polypeptide.

In certain contexts, an "antibody" refers to a protein based molecule that is naturally produced by animals in response to the presence of a protein or other molecule or that is not recognized by the animal's immune system to be a "self" molecule, i.e. recognized by the animal to be a foreign molecule and an antigen to the antibody. The immune system of the animal will create an antibody to specifically bind the antigen, and thereby targeting the antigen for elimination or degradation. It is well recognized by skilled artisans that the molecular structure of a natural antibody can be synthesized and altered by laboratory techniques. Recombinant engineering can be used to generate fully synthetic antibodies or fragments thereof providing control over variations of the amino acid sequences of the antibody. Thus, as used herein the term "antibody" is intended to include natural antibodies, monoclonal antibody, or non-naturally produced synthetic antibodies, and binding fragments, such as single chain binding fragments. These antibodies may have chemical modifications. The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same antigen. The term "monoclonal" is not limited to any particular method for making the antibody, nor is the term limited to antibodies produced in a particular species, e.g., mouse, rat, etc.

From a structural standpoint, an antibody is a combination of proteins: two heavy chain proteins and two light chain proteins. The heavy chains are longer than the light chains. The two heavy chains typically have the same amino acid sequence. Similarly, the two light chains have the same amino acid sequence. Each of the heavy and light chains contain a variable segment that contains amino acid sequences which participate in binding to the antigen. The variable segments of the heavy chain do not have the same amino acid sequences as the light chains. The variable segments are often referred to as the antigen binding domains. The antigen and the variable regions of the antibody may physically interact with each other at specific smaller segments of an antigen often referred to as the "epitope." Epitopes usually consist of surface groupings of molecules, for example, amino acids or carbohydrates. The terms "variable region," "antigen binding domain," and "antigen binding region" refer to that portion of the antibody molecule which contains the amino acid residues that interact with an antigen and confer on the antibody its specificity and affinity for the antigen. Small binding regions within the antigen-binding domain that typically interact with the epitope are also commonly alternatively referred to as the "complementarity-determining regions, or CDRs." CDRs are typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991); and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917).

"Framework Region" or "FR" residues are those variable domain residues other than the hypervariable region residues. The term antibody includes monoclonal antibodies, multi-specific antibodies, human antibodies, humanized antibodies, synthetic antibodies, chimeric antibodies, camelized antibodies, single chain antibodies, disulfide-linked Fvs (sdFv), intrabodies, and anti-idiotypic (anti-Id) antibodies. In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor, or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The term "substantially," as used in the context of binding or exhibited effect, is intended to denote that the observed effect is physiologically or therapeutically relevant. Thus, for example, a molecule is able to substantially block an activity if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete).

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize differentiated somatic cells (non-embryonic) transfected with a DNA expression vector that contains the template. The cells are cultured under conditions such that they translate the desired protein. Expressed proteins are extracted for subsequent purification. In vivo protein expression systems using prokaryotic and somatic eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation, and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASAID), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

Host cells may be co-transfected with such expression vectors, which may contain different selectable markers. The coding sequences may comprise cDNA or genomic DNA or both. The host cell used to express a polypeptide can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell and may be selected so as to have the desired expression and regulatory characteristics in the selected host cell.

The present disclosure includes nucleic acid molecules (DNA or RNA) that encode chimeric antigen receptors, antibodies, fusion proteins, or fragments, as well as vector molecules (such as plasmids) that are capable of transmitting or of replication such nucleic acid molecules and expressing such chimeric antigen receptors, antibodies, fusion proteins or fragments in a cell line. The nucleic acids can be single-stranded, double-stranded, may contain both single-stranded and double-stranded portions.

The term "variants" is contemplated to include functional variants, allelic variants, or active fragments. Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variants include those with not more than 1% or 2% of the amino acids are substituted. Variants include those with not more than 3% or 4% of the amino acids are substituted. Variants include proteins with greater than 80%, 89%, 90%, 95%, 98%, or 99% identity or similarity.

Variants can be tested by mutating the vector to produce appropriate codon alternatives for polypeptide translation. Active variants and fragments can be identified with a high probability using computer modeling. Shihab et al. report an online genome tolerance browser. BMC Bioinformatics. 2017, 18(1):20. Ng et al. report methods of predicting the effects of amino acid substitutions on protein function. Annu Rev Genomics Hum Genet. 2006, 7:61-80. Teng et al. Approaches and resources for prediction of the effects of non-synonymous single nucleotide polymorphism on protein function and interactions. Curr Pharm Biotechnol. 2008, 9(2):123-33.

Guidance in determining which and how many amino acid residues may be substituted, inserted, or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLOS Comput Biol. 2016, 12(3):e1004775; Marks et al. Protein structure from sequence variation, Nat Biotechnol. 2012, 30(11):1072-80; Mackenzie et al. Curr Opin Struct Biol. 2017, 44:161-167 Mackenzie et al. Proc Natl Acad Sci USA. 113(47):E7438-E7447 (2016); Joseph et al. J R Soc Interface. 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—ST N Q.

Methods of Treatment

In certain embodiments, this disclosure relates to methods for treating and/or preventing cancer which comprises the step of administering a galectin-9 specific binding agent or chimeric antigen receptor or vector encoding the same or a plurality of cells expressing the same as described herein, or a pharmaceutical composition as described herein to a subject.

In certain embodiments, the cells may be administered to a subject having cancer or in order to lessen, reduce or improve at least one symptom associated with cancer and/or to slow down, reduce or block the progression of cancer.

In certain embodiments, methods may involve the steps of: (i) isolating a cell-containing sample; (ii) transducing or transfecting such cells with a nucleic acid sequence or vector provided herein and (iii) administering the cells from (ii) to a subject.

In certain embodiments, this disclosure relates to uses of galectin-9 specific binding agents in methods of treating cancer such as hematological cancers or solid tumors. In certain embodiments, the galectin-9 specific binding agent is a TIM3, CD44, CD40, CLEC7a (Dectin-1), or CD137 (4-1BB) extracellular domain, or an anti-galectin-9 antibody, single chain antibody, antibody, or fragment, or binding variants thereof. In certain embodiments, cancer treatment is a cell-based therapy using chimeric antigen receptors having a galectin-9 specific targeting sequence.

In certain embodiments, the subject is overweight or obese, e.g., diagnosed with a body mass index of 25, 30, 35 or greater. In certain embodiments, the subject is less than 5, 10, or 20 years old. In certain embodiments, the subject is more than 50, 55, or 60 years old.

In certain embodiments, cancer treatment methods comprise administering an effective amount of a galectin-9 specific binding agent or immune effector cell comprising a chimeric antigen receptor containing the same to a subject in need thereof. In certain embodiments, this disclosure relates to methods of treating cancer in a subject comprising isolating immune effector cells, such as T cells, e.g., from the subject; transfecting the cells with a vector encoding a chimeric antigen receptor, wherein the chimeric antigen receptor encodes a galectin-9 specific binding agent; culturing the cells under conditions such that the galectin-9 specific binding agent is expressed on the surface of the cells; and administering an effective of amount of the cells expressing the galectin-9 specific binding agent to the subject.

In certain embodiments, chimeric antigen receptor comprises an extracellular galectin-9 specific binding agent, such as single-chain variable fragment of an antibody that specifically binds galectin-9, an extracellular hinge and spacer element, a transmembrane domain, and intracellular signaling domains that induces T-cell signaling, e.g., CD3zeta or an Fc receptor which activate T-cell effector functions for cancer cell elimination. In certain embodiments, the chimeric antigen receptor further comprises an additional signaling domain (costimulatory or accessory molecules), such as CD28, 4-1BB (CD137), OX-40, CD244, CD27, or ICOS.

In certain embodiments, chimeric antigen receptor comprising a targeting sequence of variable lymphocyte receptor domain or variant thereof, a transmembrane domain, a T cell costimulatory molecule domain, and a signal-transduction component of a T-cell antigen receptor domain such as CD3zeta (CD3Z).

In certain embodiments, the galectin-9 specific binding agent has a TIM3, CD44, CD40, CLEC7a (Dectin-1), or CD137 (4-1BB) extracellular domain amino acid sequence or fragment, or binding variants thereof. In certain embodiments, the chimeric antigen receptor comprises CD28 and CD3zeta.

In certain embodiments, the TIM3 extracellular domain has amino acid sequence

```
                                        (SEQ ID NO: 1)
SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMN

DEKFNLKLVIKPAKVTPAPTRQRDFTAAFPRMLTTRGHGPAETQTLGSL

PDINLTQISTLANELRDSRLANDLRDSGATIRIG
```

or variants thereof.

In certain embodiments, the galectin-9 specific binding agent is a single chain antibody having amino acid sequence

```
                                       (SEQ ID NO: 10)
MKCSWGIFFLLSVTAGVHSKVQLQQSGAELVKPGASVKLSCKASGYTFT

DYTIHWVKQRSGQGLEWIGWFYPGSHSIKYNEQFKDRATLTADKSSSTV

YMELSRLTSEDSAVYFCTRHGGYDGFDYWGQGTTLTVSSAKTTPPSVYP

LGGGGSGGGGSGGGGSLDGGKMDSQAQVLMLLLLWVSGTCGDIVMSQSP

SSLAVSVGEKITMSCKSSQSLFYSTNQKNYLAWYQQKPGQSPKLLIYWA

STRESGVPDRFTGSGSGTDFTLTISSVKAEDLAVYYCQQYYYFPYTFGG

GTKLEIKRADAAPTVSIFPPSS
```

or variants thereof.

In certain embodiments, the galectin-9 specific binding agent is a single chain antibody having amino acid sequence a single chain antibody having amino acid sequence (SEQ ID NO: 17)
MGWSFIILLSVTAGVHSKVQLQQSGAELVKPGASVKLSCKASGYTFTEY

TIHWVKQRSGQGLEWIGWFYPGSGSMEYNEKFDKATLTADNSSSTVYME

LSRLTSEDSAVYFCERHGGYDGFDYWGQGTTLTVSSAKTTPPSVYPLIF

LEDLLQYSQLPWKIDVLLLFSQDFQAVYGGGGSGGGGSGGGGSLDGGKM

DSQAQVLMLLLLWVSGTCGDIVMSQSPSSLAVSVGEKVTMSCKSSQSLL

YSNNQKNYLAWYQQKPGQSPKLLIYWASTRGSGVPDRFTGSGSGTDFTL

TISSVKAEDLAIYYCQQYYSYPFTFGGGTKLEIKRADAAPTVSIFPPSS or variants thereof.

In certain embodiments, this disclosure relates to nucleic acids and vectors encoding a chimeric antigen receptor wherein the chimeric antigen receptor comprises a segment which specifically binds galectin-9. In certain embodiments, this disclosure relates to vectors comprising a nucleic acid encoding a chimeric antigen receptor in operable combination with a promotor. In certain embodiments, the segment that specifically binds galectin-9 has a TIM3 extracellular domain amino acid sequence. In certain embodiments, the TIM3 extracellular domain has the amino acid sequence (SEQ ID NO: 1)
SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMN

DEKFNLKLVIKPAKVTPAPTRQRDFTAAFPRMLTTRGHGPAETQTLGSL

PDINLTQISTLANELRDSRLANDLRDSGATIRIG or variants thereof.

In certain embodiments, a polypeptide segment that specifically binds galectin-9 is a single chain antibody having amino acid sequence (SEQ ID NO: 10)
MKCSWGIFFLLSVTAGVHSKVQLQQSGAELVKPGASVKLSCKASGYTFT

DYTIHWVKQRSGQGLEWIGWFYPGSHSIKYNEQFKDRATLTADKSSSTV

YMELSRLTSEDSAVYFCTRHGGYDGFDYWGQGTTLTVSSAKTTPPSVYP

LGGGGSGGGGSGGGGSLDGGKMDSQAQVLMLLLLWVSGTCGDIVMSQSP

SSLAVSVGEKITMSCKSSQSLFYSTNQKNYLAWYQQKPGQSPKLLIYWA

STRESGVPDRFTGSGSGTDFTLTISSVKAEDLAVYYCQQYYYFPYTFGG

GTKLEIKRADAAPTVSIFPPSS or variants thereof.

In certain embodiments, a polypeptide segment that specifically binds galectin-9 is a single chain antibody having amino acid sequence a single chain antibody having amino acid sequence (SEQ ID NO: 17)
MGWSFIILLSVTAGVHSKVQLQQSGAELVKPGASVKLSCKASGYTFTEY

TIHWVKQRSGQGLEWIGWFYPGSGSMEYNEKFDKATLTADNSSSTVYME

LSRLTSEDSAVYFCERHGGYDGFDYWGQGTTLTVSSAKTTPPSVYPLIF

LEDLLQYSQLPWKIDVLLLFSQDFQAVYGGGGSGGGGSGGGGSLDGGKM

DSQAQVLMLLLLWVSGTCGDIVMSQSPSSLAVSVGEKVTMSCKSSQSLL

-continued

YSNNQKNYLAWYQQKPGQSPKLLIYWASTRGSGVPDRFTGSGSGTDFTL

TISSVKAEDLAIYYCQQYYSYPFTFGGGTKLEIKRADAAPTVSIFPPSS or variants thereof.

In certain embodiments, the signal-transduction component of the T-cell antigen receptor comprises an immunoreceptor tyrosine-based activation motif with the consensus sequence YXXLXXXXXXXXYXXL (SEQ ID NO: 30) wherein X is any amino acid L is leucine or isoleucine and optionally one or two X are optionally deleted.

In certain embodiments, the subject to be treated is diagnosed with cancer such as a metastatic or non-metastatic tumor or a hematological malignancy. Such malignancies include leukemias and lymphomas, such as acute lymphoblastic leukemia (ALL), B-cell acute lymphoblastic leukemia (B-ALL), acute myelogenous leukemia (AML), chronic lymphocytic leukemia (CLL), small lymphocytic lymphoma (SLL), chronic myelogenous leukemia (CML), acute monocytic leukemia (AMA) and/or other leukemias. In certain embodiments, the subject is diagnosed with a lymphoma such as all subtypes of Hodgkin's lymphoma or non-Hodgkin's lymphoma. In certain embodiments, the subject is diagnosed with a plasma cell malignancy such as multiple myeloma. In certain embodiments, the subject is diagnosed with breast cancer, prostate cancer, uterine cancer, lung cancer, skin cancer, stomach cancer, mouth cancer, esophageal cancer, kidney cancer (renal carcinoma), pancreatic cancer, liver cancer (hepatocellular carcinoma), gallbladder cancer, thyroid cancer, or brain cancer (neuroblastoma).

In certain embodiments, the galectin-9 specific binding agent or cells comprising a galectin-9 specific chimeric antigen receptor are administered in combination with another anticancer agent. In certain embodiments, the anticancer agent is an anti-PD-1 antibody, an anti-PD-1L antibody or an anti-CTLA-4 antibody. In certain embodiments, the anticancer agent is ipilimumab, nivolumab, pembrolizumab, cemiplimab, atezolizumab, durvalumab, avelumab, or combinations thereof.

In certain embodiments, this disclosure relates to methods of treating cancer comprising administering an effective amount of a galectin-9 specific binding agent or cells comprising a galectin-9 specific chimeric antigen receptor to a subject in need thereof. In certain embodiments, the galectin-9 specific binding agent is a protein having amino acid sequence of a TIM3, CD44, CD40, CLEC7a (Dectin-1), or CD137 (4-1BB) extracellular domain. In certain embodiments, the TIM3 extracellular domain has the amino acid sequence (SEQ ID NO: 1)
SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMN

DEKFNLKLVIKPAKVTPAPTRQRDFTAAFPRMLTTRGHGPAETQTLGSL

PDINLTQISTLANELRDSRLANDLRDSGATIRIG or variants thereof.

In certain embodiments, galectin-9 specific binding agent is an antibody (1G3) with a heavy chain having a CDR1 amino acid sequence GYTFTDYT (SEQ ID NO: 2), a CDR2 amino acid sequence FYPGSHSI (SEQ ID NO: 3) and a CDR3 amino acid sequence HGGYDGFDY (SEQ ID NO: 4), and a light chain having a CDR1 amino acid sequence QSLFYSTNQKNY (SEQ ID NO: 5), a CDR2 amino acid sequence WAST (SEQ ID NO: 6), and a CDR3 amino acid sequence QQYYYFPYT (SEQ ID NO: 7). In certain embodiments, the heavy chain has amino acid sequence (SEQ ID NO: 8)
MKCSWGIFFLLSVTAGVHSKVQLQQSGAELVKPGASVKLSCKASGYTFT
DYTIHWVKQRSGQGLEWIGWFYPGSHSIKYNEQFKDRATLTADKSSSTV
YMELSRLTSEDSAVYFCTRHGGYDGFDYWGQGTTLTVSSAKTTPPSVYP
L and the light chain has amino acid sequence (SEQ ID NO: 9)
LDGGKMDSQAQVLMLLLLWVSGTCGDIVMSQSPSSLAVSVGEKITMSCK
SSQSLFYSTNQKNYLAWYQQKPGQSPKLLIYWASTRESGVPDRFTGSGS
GTDFTLTISSVKAEDLAVYYCQQYYYFPYTFGGGTKLEIKRADAAPTVS
IFPPSS.

In certain embodiments, the antibody is a single chain antibody having amino acid sequence (SEQ ID NO: 10)
MKCSWGIFFLLSVTAGVHSKVQLQQSGAELVKPGASVKLSCKASGYTFT
DYTIHWVKQRSGQGLEWIGWFYPGSHSIKYNEQFKDRATLTADKSSSTV
YMELSRLTSEDSAVYFCTRHGGYDGFDYWGQGTTLTVSSAKTTPPSVYP
LGGGGSGGGGSGGGGSLDGGKMDSQAQVLMLLLLWVSGTCGDIVMSQSP
SSLAVSVGEKITMSCKSSQSLFYSTNQKNYLAWYQQKPGQSPKLLIYWA
STRESGVPDRFTGSGSGTDFTLTISSVKAEDLAVYYCQQYYYFPYTFGG
GTKLEIKRADAAPTVSIFPPSS or variants thereof.

In certain embodiments, the galectin-9 specific binding agent is an antibody (2E12) with a heavy chain having a CDR1 amino acid sequence GYTFTEYT (SEQ ID NO: 11), a CDR2 amino acid sequence FYPGSGS (SEQ ID NO: 12) and a CDR3 amino acid sequence HGGYDGFDY (SEQ ID NO: 4), and a light chain having a CDR1 amino acid sequence QSLLYSNNQKNY (SEQ ID NO: 13), a CDR2 amino acid sequence WAST (SEQ ID NO: 6), and a CDR3 amino acid sequence QQYYSYPFT (SEQ ID NO: 14). In certain embodiments, the heavy chain has the amino acid sequence (SEQ ID NO: 15)
MGWSFIILLSVTAGVHSKVQLQQSGAELVKPGASVKLSCKASGYTFTEY
TIHWVKQRSGQGLEWIGWFYPGSGSMEYNEKFDKATLTADNSSSTVYME
LSRLTSEDSAVYFCERHGGYDGFDYWGQGTTLTVSSAKTTPPSVYPLIF
LEDLLQYSQLPWKIDVLLLFSQDFQAVY, and the light chain has the amino acid sequence (SEQ ID NO: 16)
LDGGKMDSQAQVLMLLLLWVSGTCGDIVMSQSPSSLAVSVGEKVTMSCK
SSQSLLYSNNQKNYLAWYQQKPGQSPKLLIYWASTRGSGVPDRFTGSGS -continued

GTDFTLTISSVKAEDLAIYYCQQYYSYPFTFGGGTKLEIKRADAAPTVS
IFPPSS.

In certain embodiments, the antibody is a single chain antibody having amino acid sequence (SEQ ID NO: 17)
MGWSFIILLSVTAGVHSKVQLQQSGAELVKPGASVKLSCKASGYTFTEY
TIHWVKQRSGQGLEWIGWFYPGSGSMEYNEKFDKATLTADNSSSTVYME
LSRLTSEDSAVYFCERHGGYDGFDYWGQGTTLTVSSAKTTPPSVYPLIF
LEDLLQYSQLPWKIDVLLLFSQDFQAVYGGGGSGGGGSGGGGSLDGGKM
DSQAQVLMLLLLWVSGTCGDIVMSQSPSSLAVSVGEKVTMSCKSSQSLL
YSNNQKNYLAWYQQKPGQSPKLLIYWASTRGSGVPDRFTGSGSGTDFTL
TISSVKAEDLAIYYCQQYYSYPFTFGGGTKLEIKRADAAPTVSIFPPSS or variants thereof.

In certain embodiments, immune effector cells are $CD4^+$, $CD8^+$ T cells or combinations thereof. In certain embodiments, T cells were isolated from peripheral blood by sorting cells using human CD3+ binding agents, e.g., magnetic beads conjugated to an anti-human CD3+ antibody. In certain embodiments, immune effector cells are expanded in vitro by mixing with an interleukin such as IL-2 and then infused back into the patient. In certain embodiments, immune effector cells are expanded in vitro by mixing with IL-21 during in vitro culture. In certain embodiments the subject is administered a chemotherapy regiment that induces lymphodepletion such as cyclophosphamide, prior to cell infusion. In certain embodiments, cells are administered in combination with an interleukin such as IL-2. In certain embodiments, immune effector cells are peripheral blood mononuclear cells (PBMCs). In certain embodiments, T cells can be obtained by in vitro peptide stimulation of PBMCs collected from patients.

In certain embodiments, the chimeric antigen receptor gene construct contains a nucleic acid encoding a CAR and encoding IL-12 in operable combination with a promoter to express cytokines such as IL-12. In certain embodiments, a vector has a NFAT6 minimal promoter that initiates IL-12 transcription upon CAR-redirected T-cell activation or includes an IRES site followed by a gene encoding IL-12 in the CAR vector.

Pharmaceutical Compositions

In certain embodiments, this disclosure relates to also relates to a pharmaceutical composition containing a galectin-9 specific binding agent, or vector or a plurality of cells as described herein. The pharmaceutical composition may additionally comprise a pharmaceutically acceptable carrier, diluent, or excipient. The pharmaceutical composition may optionally comprise one or more further pharmaceutically active polypeptides and/or compounds. Such a formulation may, for example, be in a form suitable for intravenous infusion. In certain embodiments, the excipient is a saccharide or polysaccharide, sodium chloride, or pH buffering agent.

Obesity-Induced Galectin-9 is a Therapeutic Target in B-ALL

The incidence of obesity is alarming given that obesity significantly increases mortality rates in patients with various cancer subtypes including leukemia. Experiments reported herein indicate that adipocyte-secreted proteins upregulate the surface expression of galectin-9 (GAL-9) on human B-acute lymphoblastic leukemia cells (B-ALL) which promotes chemoresistance. Antibody-mediated targeting of GAL-9 on B-ALL cells inhibits the cell cycle checkpoint which promotes apoptosis in vitro and significantly extends the survival of obese mice challenged with aggressive B-ALL. These studies reveal that adipocytes directly induce the upregulation of GAL-9 on B-ALL cells, which can be targeted with antibody-based or chimeric antigen receptor-based therapies to overcome obesity-induced chemoresistance.

Adipocytes Promote Chemoresistance

Experiments were performed indicating that adipocyte-secreted factors significantly alter the phenotype (clustering) and function (induction of genes regulating intracellular signaling pathways) of human B-ALL cells. Thus, additional experiments were performed to determine how adipocyte-conditioned medium (ACM)-exposed B-ALL cells responded to chemotherapy treatment. In obese patients, leukemia cells would be exposed to an adipocyte-rich microenvironment prior to chemotherapy administration. To mimic this scenario in vitro, human B-ALL cell lines were pre-treated for 24 hours with unconditioned medium (RPMI), stromal cell-conditioned medium (SCM), or ACM prior to the addition of methotrexate (MTX) for 2 days. MTX induced significant cytotoxicity in human B-ALL cell lines in unconditioned medium, and MTX-induced cell death was not impacted by pre-conditioning with SCM. Strikingly, MTX-induced cell death was decreased by 40-70% in cultures pre-treated with ACM. Exposure to ACM also induced resistance to doxorubicin and vincristine.

In order to address the mechanism of ACM-induced chemoresistance, gene expression changes were explored in human B-ALL cells exposed to RPMI, SCM, and ACM in the presence and absence of MTX. Principal component analysis (PCA) and unsupervised hierarchical clustering of RNA-sequencing results revealed that global gene expression profiles were surprisingly similar in human B-ALL cell lines cultured in RPMI and SCM; however, ACM exposure induced dramatic changes in gene expression in leukemia cells. Changes in gene expression profiles in ACM-conditioned cultures became more evident after MTX treatment, with REH and RCH-AcV cell lines cultured in ACM clustering together and distinct from those observed in RPMI and SCM cultures. Gene ontology (GO) pathway analysis revealed the ACM alone increased the activity of pathways that modulate responses to toxic substance and leukocyte adhesion, while attenuating pathways involved in BMP binding and responses to misfolded proteins in both B-ALL cell lines tested. In response to methotrexate treatment, cellular processes were more extensively altered in ACM-exposed B-ALL cells compared to ACM conditioning alone. Notably, most of the pathways in MTX-treated ACM-exposed B-ALL cells were downregulated including those involved in cell cycle regulation/checkpoint control, DNA integrity, and the regulation of cellular activation. These results highlight the chemoresistance-inducing properties of adipocytes on human B-ALL cells and implicate pathways that may be involved in the induction of chemoresistance after exposure to adipocyte-secreted factors.

To determine the nature of the adipocyte-secreted factor that induced chemoresistance, human B-ALL cells were conditioned with nuclease, lipase, or protease-treated RPMI, SCM, or ACM prior to exposure to MTX. Protease treatment of ACM abolished its ability to confer chemoresistance to human B-ALL cells. In contrast, treatment with nucleases or lipases had no significant impact on chemo-protection conferred by ACM. Co-culturing human B-ALL cells directly with adipocytes (but not BMSC) also conferred chemoresistance to MTX and the extent of protection was not significantly different in adipocyte co-cultures compared to cultures treated with ACM. These results suggest that adipocyte-secreted proteins are largely responsible for inducing chemoresistance in human B-ALL cells. To determine if the surviving B-ALL cells maintain proliferative capacity when the drug was no longer present, human B-ALL cells were pre-conditioned with RPMI, SCM, or ACM and treated with MTX and then equal numbers of viable cells were cultured in RPMI without MTX for an additional 3 days. In these studies, cell density was significantly increased after removal of MTX in cultures of ACM-conditioned leukemia cells relative to cells conditioned with RPMI or SCM. Thus, B-ALL cells conditioned with ACM had an enhanced ability to recover from MTX treatment.

Adipocytes Upregulate Galectin-9 on B-ALL Cells

Distinctive phenotypes elicited in ACM-exposed human B-ALL cells included the upregulation of genes involved in oncogenic signaling pathways, the acquisition of chemoresistance, and induction of cellular aggregation. It is possible that these phenotypes were related; therefore, surface expression of adhesion molecules were assessed with reported signaling capabilities. Expression of 20 candidate molecules was assessed on 8 human B-ALL cell lines. Only galectin-9 (GAL-9) was significantly upregulated on the surface of every human B-ALL cell line following exposure to adipocyte-secreted factors or co-cultured with adipocytes. Minimal surface expression of GAL-9 was observed at baseline (RPMI) or in response to interactions with BMSC or SCM. Furthermore, the short and long isoforms of GAL-9 RNA (LGALS9) were significantly upregulated in ACM-exposed human B-ALL cell lines. Exposing human B-ALL cells to ACM also upregulated the HAVCR2 gene, which encodes T-cell immunoglobulin and mucin-domain containing-3 (TIM-3), the receptor for GAL-9. While surface levels of TIM-3 did not increase on ACM-exposed B-ALL cells, ACM induced significant colocalization of GAL-9 and TIM-3 on human B-ALL cells.

Given the strong induction of LGALS9 in ACM-exposed human B-ALL cell lines, publicly available databases were mined to examine the expression levels of LGALS9 and HAVCR2 in leukemia cells from patients at diagnosis and relapse. At diagnosis, the expression of LGALS9 is increased in acute myeloid leukemia (AML), B-ALL, and mixed lineage leukemia (MLL) compared to gene expression levels found in normal peripheral blood mononuclear cells (PBMCs), with samples from patients with B-ALL expressing (on average) the highest LGALS9 levels. Further analyses of B-ALL subtypes revealed varying but consistently elevated levels of LGALS9 expression in samples from patients with different subtypes of B-ALL relative to levels found in normal PBMCs. In contrast, HAVCR2 was expressed at lower levels in leukemia patient samples than observed in PBMCs. Additionally, high levels of LGALS9 expression were associated with significantly decreased overall survival in patients with relapsed B-ALL.

To examine the impact of body mass index (BMI) on GAL-9 and TIM-3 expression, PBMCs were collected from lean and obese pediatric patients at diagnosis of leukemia and RNA and surface protein levels were determined. Samples from obese patients had significantly higher levels of the short isoform of the LGALS9 mRNA compared to samples from lean patients with B-ALL. In contrast, the expression of HAVCR2 was not significantly different in B-ALL cells from lean and obese patients. In addition, both the percentage of B-ALL cells with surface expression of GAL-9 and the average level of GAL-9 surface expression were significantly increased on B-ALL cells from obese patients relative to B-ALL cells from lean patients. Surface TIM-3 was not significantly different on primary B-ALL cells isolated from lean and obese patients, consistent with the observations in B-ALL cell lines treated with ACM.

Anti-GAL-9 Antibodies are Cytotoxic to B-ALL

The significant upregulation of GAL-9 on the surface of human B-ALL cells are coincident with the induction of chemoresistance in the presence of adipocytes or ACM. Furthermore, GAL-9 is significantly increased on the surface of B-ALL cells from obese patients, and poorer prognoses were observed in patients with B-ALL expressing high levels of GAL-9, suggesting that GAL-9 functions to promote B-ALL survival in the context of obesity. To test this hypothesis, experiments were performed to determine whether treatment with an anti-galectin-9 (αGAL-9) antibody altered B-ALL phenotypes and viability.

A prominent phenotype observed in human B-ALL cells after exposure to ACM was extensive cellular clustering. Strikingly, treatment with an anti-GAL-9 antibody prevented ACM-induced cellular aggregation in every human B-ALL cell line tested with the most notable inhibition of aggregation occurring in REH cells. Moreover, combining an anti-GAL-9 antibody and MTX treatment resulted in substantial cytotoxicity in human B-ALL cells (FIG. 1). Surprisingly, single-agent anti-GAL-9 antibody administration was superior to single-agent MTX treatment when B-ALLs were exposed to ACM where, in most cases, over 90% cell death was achieved. Interestingly, anti-GAL-9 antibody treatment did not induce substantial cell death in B-ALL cells cultured in unconditioned medium or SCM, and the amount of cell death was similar to IgG treatment in all tested conditions. Thus, human B-ALL cells exposed to adipocyte-secreted factors become dependent on GAL-9 for survival and inhibition of GAL-9 on B-ALL cells in an adipocyte-rich microenvironment induces extensive leukemia cell death.

In non-malignant B-cells, GAL-9 organizes the immunoglobulin M (IgM) and B-cell Receptor (BCR) into large clusters and facilitates their ligation with the inhibitory molecules CD45 and CD22, thus attenuating B-cell activation. Experiments were performed to determine whether GAL-9 prevents the hyperactivation of B-ALL after exposure to ACM and if antibody inhibition of GAL-9 would promote activation induced cell death (AICD) in ACM-exposed B-ALL cells. Indeed, treatment with anti-GAL-9 antibody in the presence of ACM induced a significant accumulation of B-ALL cells in G2/M phases of the cell cycle, and alterations in cell cycle progression were accompanied by a complete ablation of cell cycle regulators (CDK4 and CCD3) and increased DNA damage (cleaved PARP and γH2AX levels). The induction of DNA damage was significantly less extensive when human B-ALL cells were treated with an anti-GAL-9 antibody in the presence of unconditioned medium or SCM. These results indicate that GAL-9 is a critical cell cycle regulator in B-ALL cells after ACM exposure. Consequently, antibody-mediated inhibition of GAL-9 on ACM-exposed B-ALL cells induces inappropriate cell cycle progression culminating in extensive DNA damage and cell death.

Anti-GAL-9 Immunotherapy Protects Obese Mice with B-ALL

Figure 3A:
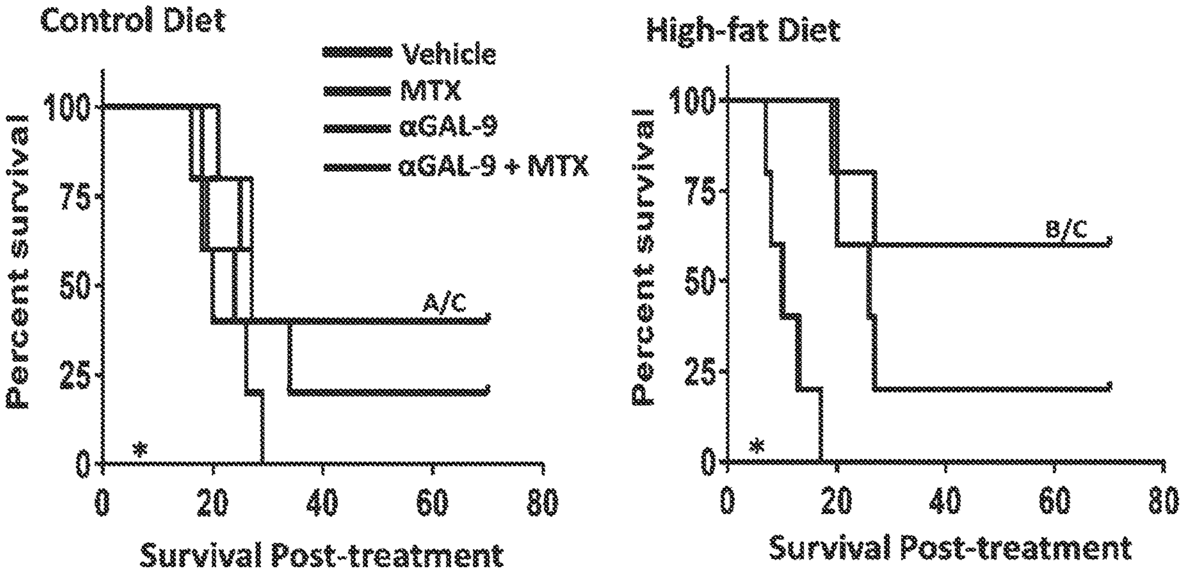
FIG. 3A shows data indicating anti-galectin-9 treatment prolongs survival in obese mice challenged with B-ALL. Lean and obese mice were inoculated intravenously with murine Bcr-Abl+Arf−/−B-ALL cells (mB-ALL). On day 7 post-inoculation, when GFP+ leukemic blasts were detected in the peripheral blood, treatment with DMSO (Vehicle, n=10), 0.75 mg/kg methotrexate (MTX, n=10), 1.5 mg/kg anti-galectin-9 antibody (αGAL-9 Ab, n=10), or (MTX+αGAL-9 Ab) a combined was initiated. Treatments were administered once weekly. Survival was monitored and significance was determined using the log-rank test with “A” representing a statistically significant difference between vehicle and MTX-treated mice, “B” between vehicle and anti-Gal-9 treated groups, and “C” between vehicle and MTX+anti-Gal-9 treated mice.
Figure 3B:
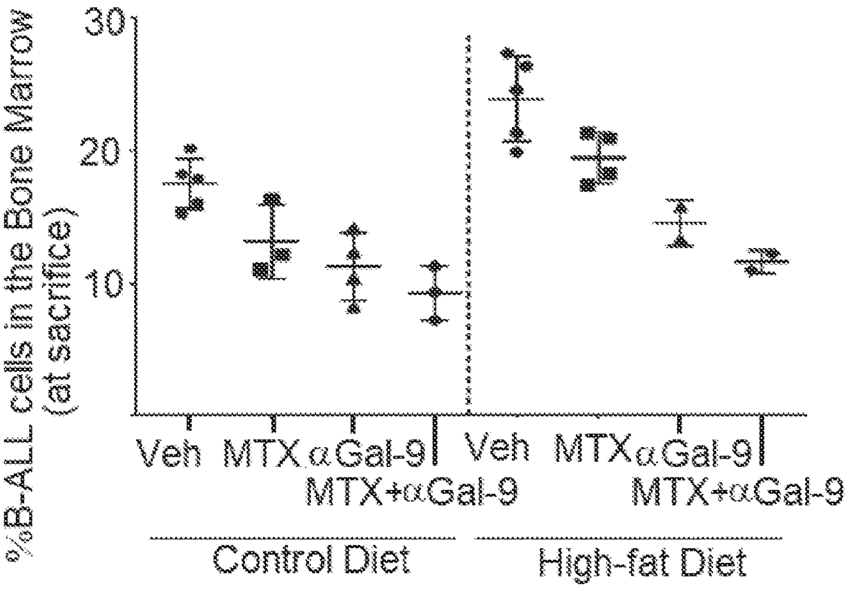
FIG. 3B shows data on the percentage of GFP+ leukemia cells in the bone marrow in lean and obese mice that were removed from study was determined by flow cytometric analysis.
Figure 4:
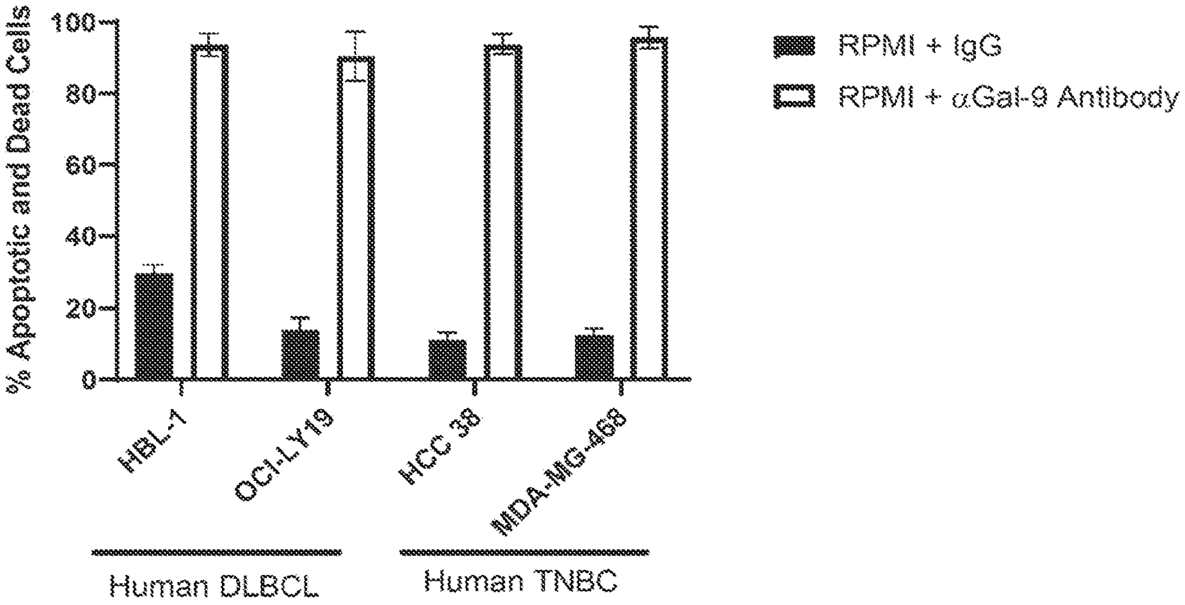
FIG. 4 shows data indicating galectin-9 inhibition is cytotoxic to human diffuse large B-cell lymphoma (DLBCL) and triple-negative breast cancer (TNBC) cells. Human DLBCL (HBL-1 and OCI-LY19) and human TNBC (HCC38 and MDA-MG-468) cell lines were cultured in unconditioned media (RPMI) with control immunoglobulin (Ctrl IgG) or with anti-galectin-9 antibody for 24 hours. After the treatment period, cells were harvested and stained with Annexin-V/PI to determine the percentage of dead and dying cells (indicated in the box).

A murine BCR-ABL+Arf−/−B-ALL (mB-ALL) model was used to test whether treatment with anti-GAL-9 antibody could be used as a therapy to treat obese mice with B-ALL. Similar to human B-ALL cells, ACM also induced chemoresistance to methotrexate and doxorubicin in mB-ALL cell cultures, validating their utility for these studies. C57BL/6 mice were maintained on lean and high-fat diets as previously described and then challenged with mB-ALL. Treatment with vehicle, MTX, anti-GAL-9 antibody, or a combination of MTX and anti-GAL-9 antibody was initiated on day 7 after leukemia inoculation, when GFP+B-ALL cells were detected in the peripheral blood. All drug combinations were well-tolerated in lean mice; however, obese mice loss substantial weight when treated with MTX alone. The significant amount of weight loss observed in obese mice was mitigated with single agent anti-GAL-9 antibody treatment alone and when combined with MTX administration suggesting that anti-GAL-9 antibody treatment strategies improve drug tolerability in obese mice with B-ALL. MTX significantly extended the survival of lean mice challenged with mB-ALL relative to mice receiving the vehicle control (FIG. 3A). In contrast, anti-GAL-9 single agent treatment did not significantly extend survival in lean mice relative to vehicle-treated mice (FIG. 3A). Furthermore, the survival of lean mice receiving the combination treatment of MTX and anti-GAL-9 antibody was equivalent to lean mice receiving the single agent MTX regimen (FIG. 3A). Despite similar survival outcomes, the leukemia burden in euthanized moribund mice varied between treatment groups. Notably, lean mice receiving the combination treatment had the lowest detectable leukemia levels in the bone marrow at the time of sacrifice (FIG. 3B).

Leukemogenesis was accelerated in mice fed high-fat diets, as indicated by the observation that vehicle-treated obese mice succumbed to mB-ALL by day 17 post-challenge; whereas vehicle-treated lean mice succumbed to mB-ALL by day 29 post-challenge. Furthermore, the leukemia burden in the bone marrow of obese mice that were euthanized due to signs of morbidity was significantly higher than in lean mice (FIG. 3B). In contrast to lean mice, treatment with single agent anti-GAL-9 antibody significantly prolonged survival in obese mice with approximately 60% of mice surviving past 3 months of challenge with mB-ALL. Unlike the protection observed in lean mice treated with MTX, obese mice treated with MTX were not significantly protected relative to vehicle-treated mice. The combination of MTX and anti-GAL-9 antibody treatment in obese mice with mB-ALL did not augment survival over single-agent anti-GAL-9 antibody treatment suggesting that the significant extension in survival observed in obese mice was mainly attributable to anti-GAL-9 antibody treatment.

Targeting Galectin-9 Positive Malignancies with Natural Receptor-Based Galectin-9 Directed CAR T-Cells Obesity rates are rising worldwide and will continue to impose a burden on global healthcare systems given its association with multiple diseases including hematological malignancies. Obesity increases mortality rates associated with blood borne and solid tumors; therefore, finding therapeutic strategies/targets will be important for improving outcomes in these patients. Importantly, galectin-9 is highly expressed on the surface of DLBCL and T-ALL cells and is upregulated on the surface of B-ALL cells in overweight and obese microenvironments. Additionally, high gene expression levels of galectin-9 in breast cancer is associated with significantly decreased survival. In obese mice with B-ALL, antibody-mediated targeting of galectin-9 results in a significant extension of survival relative to mice treated with methotrexate (MTX). Furthermore, galectin-9 antibody treatment did not induce toxicity in mice compared to MTX treatment. Galectin-9 directed CAR T-cells may protect against leukemia, lymphoma, and galectin-9 expressing solid tumors.

Galectin-9-Directed Chimeric Antigen Receptors

Chimeric antigen receptors (CARs) are proteins which fuse a specific binding domain to the effector function of a T-cell. Their usual form is that of a type I transmembrane domain protein with an antigen recognizing amino terminus, a spacer, a transmembrane domain all connected to an intracellular domain which transmits T-cell survival and activation signals.

Specific binding domains may be single-chain variable fragments (scFv) derived from monoclonal antibodies which recognize a target antigen, fused via a spacer and a transmembrane domain to a signalling intracellular domain. Such molecules result in activation of the T-cell in response to recognition by the scFv of its target. When T cells express such a CAR, they recognize and kill target cells that express the target antigen. CAR-encoding nucleic acids may be transferred into T-cells using, for example, retroviral vectors. In this way, a large number of cancer-specific T-cells can be generated for adoptive cell transfer.

The target binding domain of a CAR is typically fused via a spacer and transmembrane domain to an intercellular domain, which comprises or associates with an intracellular T-cell signaling domain. When the CAR binds the target cell this results in the transmission of an activating signal to the T-cell it is expressed on. The transmembrane domain is the sequence of a CAR that spans the membrane. It may comprise a hydrophobic alpha helix. The transmembrane domain may be derived from CD28, which provides stability.

The intercellular domain is the portion of the CAR involved in signal-transmission. The intercellular domain either comprises or associates with an intracellular T-cell signaling domain. After target bind recognition, receptors cluster, and a signal is transmitted to the cell. The most commonly used T-cell signaling component is that of CD3-zeta. This transmits an activation signal to the T-cell after the target is bound. CD3-zeta may not provide a fully competent activation signal and additional co-stimulatory signaling may be included.

The CAR may comprise a signal peptide so that when the CAR is expressed inside a cell, such as a T-cell, the nascent protein is directed to the endoplasmic reticulum and subsequently to the cell surface, where it is expressed. The CAR may comprise a spacer sequence to connect the target binding domain with the transmembrane domain and spatially separate the cell binding domain from the intracellular domain. A flexible spacer allows to the cell-binding domain to orient in different directions to enable cell binding.

The spacer sequence may, for example, comprise an IgG1 Fc region, an IgG1 hinge or a CD8 stalk, or a combination thereof. The linker may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

In certain embodiments, the immune effector cell reported herein may be lymphocytes, such as cytotoxic T lymphocytes (CTL), T helper cells, lymphokine-activated cells, tumor-infiltrating lymphocytes (TILS), NK cells, naive cells, memory cells, gamma delta T cells, natural killer (NK) cells as well as cell populations comprising variable quantities of one or more of the aforesaid cells.

In a preferred embodiment, the lymphocytes are CTLs. CTLs express the CD8 at their surface and destroy infected cells and tumor cells. These cells recognize their targets by binding to antigen associated with MHC class I, which is present on the surface of nucleated cells. Suitable methods for obtaining CTLs for subsequent expansion in vitro using the method of the disclosure are extensively known to an expert in the art and include, without limitation, isolation from peripheral blood, from umbilical cord blood, from tissues containing lymphocytes. In certain embodiments, the lymphocytes are isolated through drainage from the lymph nodes of patients suffering from a particular disease.

Once the lymphocytes have been isolated, they are placed in contact with a composition of the disclosure, a chimeric antigen receptor of the disclosure, an antibody or polynucleotide of the disclosure, a vector of the disclosure, a gene construct of the disclosure or a host cell of the disclosure in suitable conditions for lymphocyte expansion to take place. Typically, contacting the lymphocytes with the composition, chimeric antigen receptor, polynucleotide, vector, gene construct or host cell of the disclosure is carried out by means of culturing the lymphocytes in a suitable medium for said cells. The cells may be cultured under conventional conditions in a suitable medium for growing lymphocytes which include a Minimum Essential Medium or RPMI 1640 Medium. With a view to promoting cell growth, necessary proliferation and viability factors may be added including serum, for example, fetal calf serum or human serum and antibiotics, for example, penicillin, streptomycin. The lymphocytes are kept in the necessary conditions for supporting growth, for example, at a suitable temperature of about 37° C. and atmosphere, for example, air plus 5% $CO_2$.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

T lymphocytes are obtained from a patient by leukapheresis. CD3 is expressed on all T cells as it is associated with the T cell receptor (TCR). The majority of TCR are made up of alpha beta chains (alpha beta T-cells). T cells may be isolated and separated from a human sample (blood or PBMCs) based on the expression of alpha beta T cell receptor (TCR), gamma delta T cell receptor, CD2, CD3, CD4, CD8, CD4 and CD8, NK1.1, CD4, CD25 or combinations based on positive or negative selection.

Various T cell subsets isolated from the patient can be transduced with a vector for CAR expression. For example, central memory T cell can be isolated from peripheral blood mononuclear cells (PBMC) by selecting for CD45RO+/CD62L+ cells. The cells enriched for T cells can be activated with anti-CD3 and anti-CD28 antibodies, transduced with, for example, a lentiviral vector that directs the expression of a CAR. The activated/genetically modified T cells can be expanded in vitro with IL-2 and/or IL-15 and then cryopreserved.

The CAR cells may be any of the cell types mentioned above. Cells expressing the CAR may either be created ex vivo either from a patient's own peripheral blood (1st party), or in the setting of a hematopoietic stem cell transplant from donor peripheral blood (2nd party), or peripheral blood from an unconnected donor (3rd party).

Figure 5:
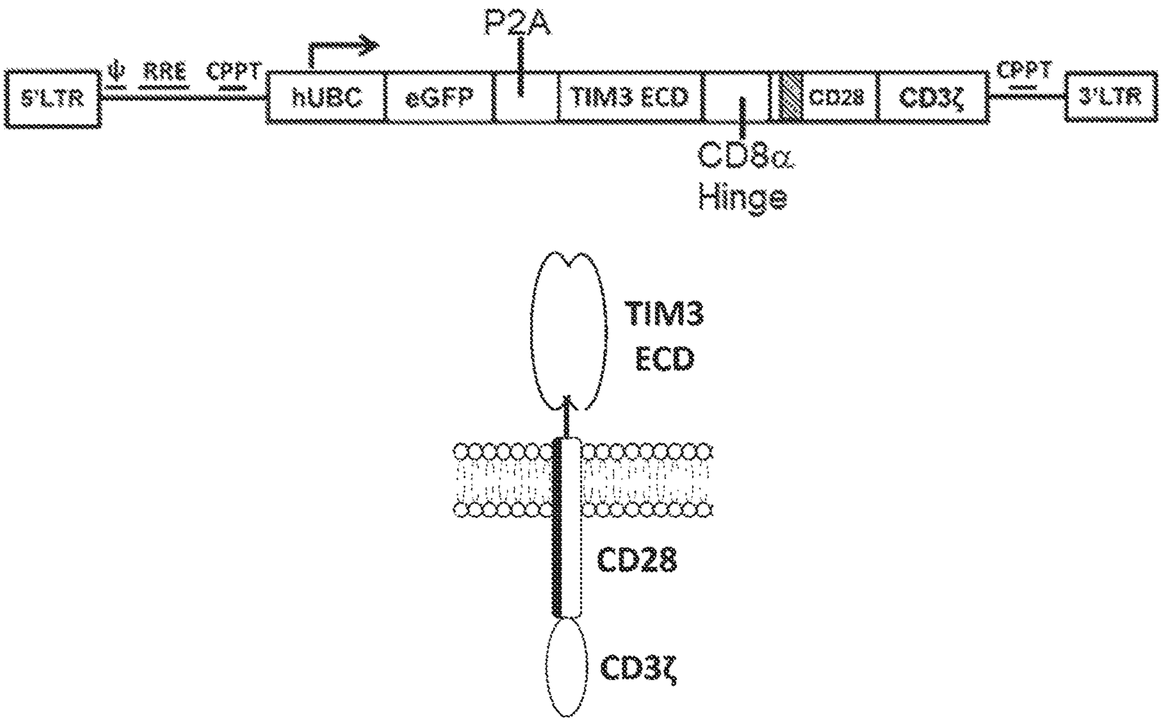
FIG. 5 illustrates a vector and CAR structure targeting Galectin-9 using the TIM3 extracellular domain (ECD).
Figure 6:
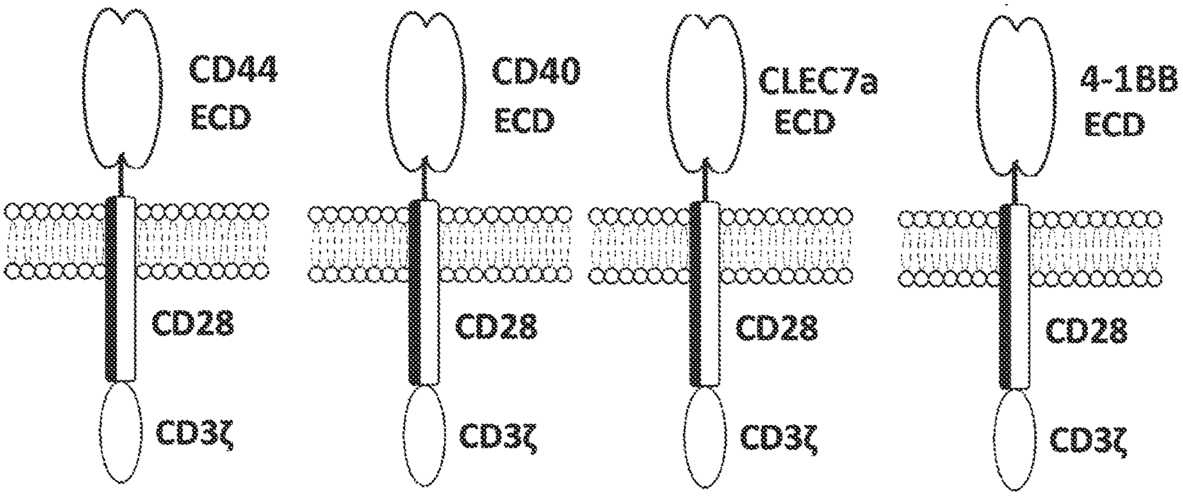
FIG. 6 illustrates a CAR structure targeting galectin-9 using CD44, CD40, CLEC7a (Dectin-1), and CD137 (4-1BB) extracellular domains.
Figure 7:
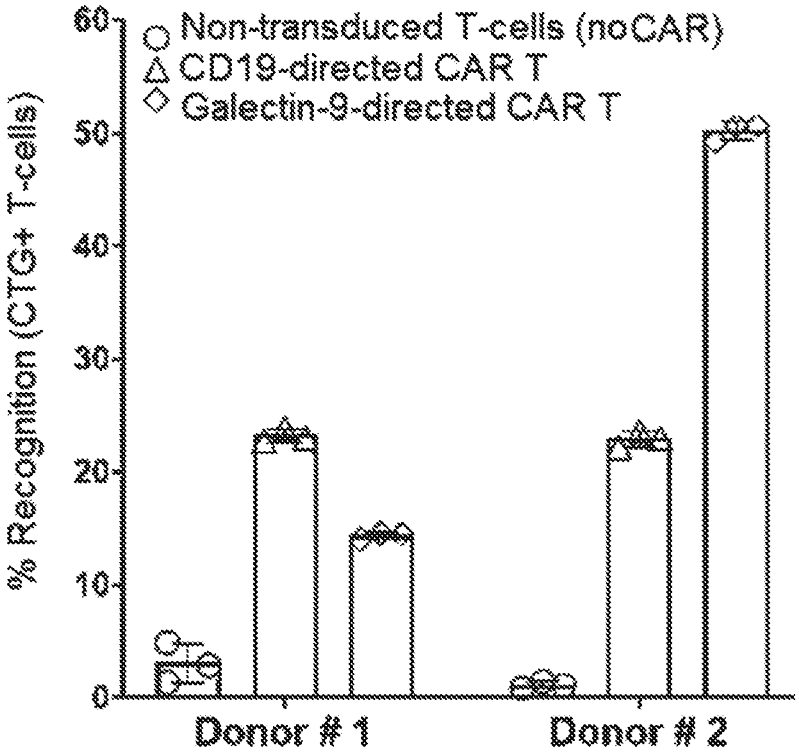
FIG. 7 shows data indicating Galectin-9-directed CAR T-cells recognized human B-ALL cells better than CD19-directed CAR T-cells. T-cells were purified from healthy donors (PBMCs) and transduced to express 2$^{nd}$ generation CARs directed against CD19 or Galectin-9 (using the TIM3 extracellular domain). Trogocytosis (also known and TRAP) assays were used to determine CAR/antigen recognition (CD19 or Gal-9) by co-culturing unlabeled CAR T-cells with cell tracker green (CTG)-labeled human B-ALL cells. After 24 hours of culture, the percentage of labeled CTG-labeled CAR T-cells (positive based on membrane transfer) was determined via flow cytometry analysis.

Gal9 CAR Structure:

FIGS. 5 and 6 illustrate galectin-9 CAR structures, e.g., IL-2 signal peptide+AscI restriction site+Gal9 binding domain sequence+NheI restriction site+CD8 alpha hinge+CD28 transmembrane and intracellular domain+CD3zeta intracellular signaling domain (bold indicates domains for the below cDNA and amino acid sequences).

cDNA sequence (SEQ ID NO: 22)

ATGTACAGGATGCAACTCCTGTCTTGCATTGCACTAAGTCTTGCACTTGTCACGAATT

CGGGCGCGCCT *Gal9_binding_domain*

(SEQ ID NO: 23)

GCTAGCACCACTACCCCGGCCCCTAGGCCCCCTACTCCAGCGCCAACTATAGCATC

ACAGCCTTTGAGCTTGAGGCCCGAAGCTTGCAGACCGGCGGCAGGGGGGGCTGTGC

ATACAAGGGGCCTCGACTTTGCCTGCGACATCGATAATGAGAAGAGCAATGGAAC

CATTATCCATGTGAAAGGGAAACACCTTTGTCCAAGTCCCCTATTTCCCGGACC

TTCTAAGCCCTTTTGGGTGCTGGTGGTGGTTGGTGGAGTCCTGGCTTGCTATA

GCTTGCTAGTAACAGTGGCCTTTATTATTTTCTGGGTGAGGAGTAAGAGGAGC

AGGCTCCTGCACAGTGACTACATGAACATGACTCCCAGGAGGCCTGGGCCAAC

CCGCAAGCATTACCAGCCCTATGCCCCACCACGCGACTTCGCAGCCTATCGCT

CCAGCAGGAGCGCAGACGCTCCCGCGTACCAGCAGGGCCAGAACCAGCTCTATAAC

GAGCTCAATCTAGGACGAAGAGAGGAGTACGATGTTTTGGACAAGAGACGTGGCCG

GGACCCTGAGATGGGAGGCAAGCCGAGAAGGAAGAACCCTCAGGAAGGCCTGTAC

AATGAACTGCAGAAAGATAAGATGGCGGAGGCCTACAGTGAGATTGGGATGAAAG

GCGAGCGCCGGAGGGGCAAGGGGCACGATGGCCTTTACCAGGGTCTCAGTACAGCC

ACCAAGGACACCTACGACGCCCTTCACATGCAGGCCCTGCCTCCTCGC.

Amino acid sequence (SEQ ID NO: 24)

MYRMQLLSCIALSLALVINSGAP *Gal9_binding_domain*

(SEQ ID NO: 25)

ASTTTPAPRPPTPAPTIASQPLSLRPEACRPAAGGAVHTRGLDFACDIDNEKSNGTIIHVK

GKHLCPSPLFPGPSKPFWVLVVVGGVLACYSLLVTVAFIIFWVRSKRSRLLHSDYM

NMTPRRPGPTRKHYQPYAPPRDFAAYRSSRSADAPAYQQGQNQLYNELNLGRREEY

DVLDKRRGRDPEMGGKPRRKNPQEGLYNELQKDKMAEAYSEIGMKGERRRGKGHDG

LYQGLSTATKDTYDALHMQALPPR

TIM3 ligand

Gal9 binding domain - TIM3 extracellular region sequence - 181 AA (SEQ ID NO: 1)

SEVEYRAEVGQNAYLPCFYTPAAPGNLVPVCWGKGACPVFECGNVVLRTDERDVNYW

TSRYWLNGDFRKGDVSLTIENVTLADSGIYCCRIQIPGIMNDEKFNLKL VIKPAKVTPAPT

RQRDFTAAFPRMLTTRGHGPAETQTLGSLPDINLTQISTLANELRDSRLANDLRDSGATI

RIG

TIM3 cDNA sequence - codon optimized - 543 bp (SEQ ID NO: 18)

TCCGAAGTAGAATACCGGGCTGAGGTAGGTCAAAATGCGTACTTGCCATGCTTCTAT

ACCCCGGCAGCACCGGGAAACCTTGTGCCAGTGTGCTGGGGTAAAGGAGCTTGCCC

CGTTTTTGAGTGTGGCAATGTAGTGTTGCGCACCGATGAACGAGATGTTAATTATTG

-continued

GACCAGCCGGTATTGGCTTAATGGTGACTTTAGGAAAGGCGATGTCTCCCTCACTAT

CGAGAATGTGACATTGGCCGACAGCGGAATCTATTGCTGTCGAATTCAAATACCCGG

TATCATGAATGACGAGAAGTTCAATCTTAAATTGGTTATCAAACCAGCCAAGGTGAC

TCCGGCACCCACTAGGCAACGAGACTTTACGGCAGCATTCCCCCGGATGCTCACGAC

TCGCGGTCACGGACCTGCCGAAACACAGACTCTTGGTTCTCTTCCTGACATTAACCT

GACCCAGATTTCCACACTTGCCAACGAGCTCCGCGACTCCAGACTCGCTAATGACCT

GCGCGATTCAGGAGCTACTATAAGAATCGGT mAb 1G3 scFv CAR
Gal9 binding domain - mAb 1G3 scFv sequence - 316 AA
(SEQ ID NO: 10)
MKCSWGIFFLLSVTAGVHSKVQLQQSGAELVKPGASVKLSCKASGYTFTDYTIHWVKQ

RSGQGLEWIGWFYPGSHSIKYNEQFKDRATLTADKSSSTVYMELSRLTSEDSAVYFCTR

HGGYDGFDYWGQGTTLTVSSAKTTPPSVYPLGGGGSGGGGSGGGGSLDGGKMDSQAQ

VLMLLLLWVSGTCGDIVMSQSPSSLAVSVGEKITMSCKSSQSLFYSTNQKNYLAWYQQ

KPGQSPKLLIYWASTRESGVPDRFTGSGSGTDFTLTISSVKAEDLAVYYCQQYYYFPYTF

GGGTKLEIKRADAAPTVSIFPPSS mAb 1G3 VH - 148 AA - 444 bp
(SEQ ID NO: 8)
MKCSWGIFFLLSVTAGVHSKVQLQQSGAELVKPGASVKLSCKASGYTFTDYTIHWVKQ

RSGQGLEWIGWFYPGSHSIKYNEQFKDRATLTADKSSSTVYMELSRLTSEDSAVYFCTR

HGGYDGFDYWGQGTTLTVSSAKTTPPSVYPL mAb 1G3 VL - 153 AA - 459 bp
(SEQ ID NO: 9)
LDGGKMDSQAQVLMLLLLWVSGTCGDIVMSQSPSSLAVSVGEKITMSCKSSQSLFYSTN

QKNYLAWYQQKPGQSPKLLIYWASTRESGVPDRFTGSGSGTDFTLTISSVKAEDLAVYY

CQQYYYFPYTFGGGTKLEIKRADAAPTVSIFPPSS

Linker sequence (G4S)3 - 15 AA - 45 bp
(SEQ ID NO: 19)
GGGGSGGGGSGGGGS mAb 1G3 scFv sequence cDNA sequence - codon optimized - 948 bp
(SEQ ID NO: 20)
ATGAAGTGTAGCTGGGGGATCTTTTTTCTTCTCAGTGTCACTGCAGGAGTGCATTCA

AAAGTCCAACTTCAGCAATCAGGAGCAGAACTGGTAAAACCGGGCGCCTCAGTTAA

ACTCAGTTGCAAAGCTAGTGGGTACACCTTCACAGATTATACGATTCACTGGGTAAA

GCAGAGGAGTGGACAAGGTTTGGAGTGGATCGGCTGGTTTTATCCCGGAAGTCACT

CAATTAAATACAACGAACAGTTCAAGGATAGAGCTACGTTGACCGCTGACAAATCC

TCTTCAACGGTATATATGGAGCTTTCAAGGCTTACATCCGAAGATTCAGCAGTCTAT

TTTTGCACCAGGCACGGTGGTTACGACGGATTCGATTATTGGGGCCAGGGAACTACT

CTGACAGTGTCATCTGCGAAAACAACTCCACCGAGTGTTTATCCTCTTGGCGGCGGA

GGGAGTGGTGGTGGCGGATCTGGGGGAGGTGGATCCCTCGACGGCGGAAAAATGGA

TTCACAGGCGCAAGTCTTGATGTTGTTGTTGCTGTGGGTATCCGGCACCTGTGGCGA

CATCGTCATGTCCCAGTCTCCTTCCTCTCTTGCAGTTTCAGTAGGGGAAAAAATAAC

AATGTCCTGTAAAAGTAGTCAGTCCCTCTTCTACAGTACAAACCAGAAAAACTATCT

GGCATGGTATCAGCAAAAACCGGGCCAGTCACCCAAACTGTTGATCTATTGGGCTTC

TACAAGGGAGAGCGGTGTGCCCGACAGGTTCACTGGCTCTGGTAGTGGCACAGATT

TTACGCTGACGATATCATCTGTCAAGGCTGAGGACCTCGCGGTCTATTACTGTCAGC

-continued

AATACTACTATTTTCCATATACTTTTGGTGGTGGAACAAAACTGGAGATTAAGCGGG

CTGATGCAGCACCAACGGTTAGTATATTTCCACCGTCTAGT mAb 2E12 scFv CAR
Gal9 binding domain - mAb 2E12 scFv sequence - 343 AA - 1029 bp
(SEQ ID NO: 17)
MGWSFIILLSVTAGVHSKVQLQQSGAELVKPGASVKLSCKASGYTFTEYTIHWVKQRSG

QGLEWIGWFYPGSGSMEYNEKFDKATLTADNSSSTVYMELSRLTSEDSAVYFCERHGG

YDGFDYWGQGTTLTVSSAKTTPPSVYPLIFLEDLLQYSQLPWKIDVLLLFSQDFQAVYG

GGGSGGGGSGGGGSLDGGKMDSQAQVLMLLLLWVSGTCGDIVMSQSPSSLAVSVGEK

VTMSCKSSQSLLYSNNQKNYLAWYQQKPGQSPKLLIYWASTRGSGVPDRFTGSGSGTD

FTLTISSVKAEDLAIYYCQQYYSYPFTFGGGTKLEIKRADAAPTVSIFPPSS.

mAb 2E12 VH - 175 AA - 525 bp
(SEQ ID NO: 15)
MGWSFIILLSVTAGVHSKVQLQQSGAELVKPGASVKLSCKASGYTFTEYTIHWVKQRSG

QGLEWIGWFYPGSGSMEYNEKFDKATLTADNSSSTVYMELSRLTSEDSAVYFCERHGG

YDGFDYWGQGTTLTVSSAKTTPPSVYPLIFLEDLLQYSQLPWKIDVLLLFSQDFQAVY mAb 2E12 VL - 153 AA - 459 bp
(SEQ ID NO: 16)
LDGGKMDSQAQVLMLLLLWVSGTCGDIVMSQSPSSLAVSVGEKVTMSCKSSQSLLYSN

NQKNYLAWYQQKPGQSPKLLIYWASTRGSGVPDRFTGSGSGTDFTLTISSVKAEDLAIY

YCQQYYSYPFTFGGGTKLEIKRADAAPTVSIFPPSS

Linker Sequence (G4S)3 (SEQ ID NO: 19)—15 AA-45 bp

Gal9 CAR3 binding domain cDNA sequence - codon optimized - 1029 bp
(SEQ ID NO: 21)
ATGGGTTGGTCATTTATTATTCTTCTCTCAGTAACAGCGGGAGTCCACT

CCAAGGTACAGCTGCAACAGTCTGGCGCGGAGCTCGTAAAACCAGGGGC

TTCTGTGAAGTTGTCTTGTAAAGCGTCAGGGTATACTTTCACCGAATAC

ACGATCCACTGGGTGAAGCAGAGGAGCGGGCAAGGCCTGGAGTGGATCG

GCTGGTTCTACCCCGGGTCAGGGTCCATGGAGTACAATGAAAAATTTGA

TAAAGCGACTCTCACAGCCGACAATAGTTCCAGCACGGTCTATATGGAA

CTTTCTCGGTTGACATCCGAGGACTCAGCCGTATATTTTTGTGAGCGCC

ACGGAGGATACGATGGGTTTGATTATTGGGGACAGGGGACTACGCTCAC

GGTGAGTTCCGCTAAGACTACTCCACCTAGTGTGTACCCACTGATCTTC

CTCGAAGACCTCTTGCAGTACTCACAACTTCCGTGGAAAATTGACGTGT

TGCTTTTGTTTAGCCAGGACTTTCAAGCTGTCTATGGGGGAGGCGGAAG

CGGAGGAGGTGGTAGTGGAGGCGGGGGGTCACTGGATGGGGGTAAAATG

GATTCACAAGCTCAGGTACTTATGCTCCTTCTGTTGTGGGTGTCCGGGA

CTTGTGGGGACATCGTCATGTCACAAAGCCCATCTAGTCTGGCCGTTTC

AGTAGGGGAAAAGGTGACTATGTCTTGCAAAAGCAGCCAAAGCTTGCTC

-continued

TATAGTAATAACCAAAAGAATTACCTCGCATGGTACCAGCAAAAGCCAG

GGCAATCTCCTAAACTGTTGATCTACTGGGCTTCAACTCGGGGTAGTGG

TGTGCCCGACCGGTTCACGGGAAGCGGGAGCGGAACAGATTTCACCCTC

ACAATTTCATCTGTGAAAGCTGAGGACCTTGCCATCTATTACTGTCAAC

AGTACTACTCATATCCCTTCACGTTCGGCGGTGGCACAAAGCTCGAAAT

CAAGAGAGCGGACGCTGCACCTACTGTAAGCATTTTTCCTCCCTCTTCC

CD44

Extracellular Domain (SEQ ID NO: 26)
TCRFAGVFHVEKNGRYSISRTEAADLCKAFNSTLPTMAQMEKALSIGFE

TCRYGFIEGHVVIPRIHPNSICAANNTGVYILTSNTSQYDTYCFNASAP

PEEDCTSVTDLPNAFDGPITITIVNRDGTRYVQKGEYRTNPEDIYP

CD40

Extracellular Domain (SEQ ID NO: 27)
EPPTACREKQYLINSQCCSLCQPGQKLVSDCTEFTETECLPCGESEFLD

TWNRETHCHQHKYCDPNLGLRVQQKGTSETDTICTCEEGWHCTSEACES

CVLHRSCSPGFGVKQIATGVSDTICEPCPVGFFSNVSSAFEKCHPWTSC

ETKDLVVQQAGTNKTDVVCGPQDRLR

CLEC7A (Dectin-1)
Extracellular Domain (SEQ ID NO: 28)
TMAIWRSNSGSNTLENGYFLSRNKENHSQPTQSSLEDSVTPTKAVKTTG
VLSSPCPPNWIIYEKSCYLFSMSLNSWDGSKRQCWQLGSNLLKIDSSNE
LGFIVKQVSSQPDNSFWIGLSRPQTEVPWLWEDGSTFSSNLFQIRTTAT
QENPSPNCVWIHVSVIYDQLCSVPSYSICEKKFSM CD137 (4-1BB)
Extracellular Domain (SEQ ID NO: 29)
LQDPCSNCPAGTFCDNNRNQICSPCPPNSFSSAGGQRTCDICRQCKGVF
RTRKECSSTSNAECDCTPGFHCLGAGCSMCEQDCKQGQELTKKGCKDCC
FGTFNDQKRGICRPWTNCSLDGKSVLVNGTKERDVVCGPSPADLSPGAS
SVTPPAPAREPGHSPQ.

The invention claimed is:

1. A vector comprising nucleic acid encoding a chimeric antigen receptor wherein the chimeric antigen receptor comprises polypeptide segment that specifically binds galectin-9, having a TIM3 extracellular domain amino acid sequence of (SEQ ID NO: 1)

SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMN

DEKFNLKLVIKPAKVTPAPTRQRDFTAAFPRMLTTRGHGPAETQTLGSL

PDINLTQISTLANELRDSRLANDLRDSGATIRIG.

2. A non-embryonic cell comprising a vector of claim 1.

* * * * *

SEQUENCE LISTING

<160> NUMBER OF SEQ ID NOS: 30

<210> SEQ ID NO 1
<211> LENGTH: 181
<212> TYPE: PRT
<213> ORGANISM: Artificial
<220> FEATURE:
<223> OTHER INFORMATION: Synthetic construct

<400> SEQUENCE: 1

Ser Glu Val Glu Tyr Arg Ala Glu Val Gly Gln Asn Ala Tyr Leu Pro
1 5 10 15

Cys Phe Tyr Thr Pro Ala Ala Pro Gly Asn Leu Val Pro Val Cys Trp
20 25 30

Gly Lys Gly Ala Cys Pro Val Phe Glu Cys Gly Asn Val Val Leu Arg
35 40 45

Thr Asp Glu Arg Asp Val Asn Tyr Trp Thr Ser Arg Tyr Trp Leu Asn
50 55 60

Gly Asp Phe Arg Lys Gly Asp Val Ser Leu Thr Ile Glu Asn Val Thr
65 70 75 80

Leu Ala Asp Ser Gly Ile Tyr Cys Cys Arg Ile Gln Ile Pro Gly Ile
85 90 95

Met Asn Asp Glu Lys Phe Asn Leu Lys Leu Val Ile Lys Pro Ala Lys
100 105 110

Val Thr Pro Ala Pro Thr Arg Gln Arg Asp Phe Thr Ala Ala Phe Pro
115 120 125

Arg Met Leu Thr Thr Arg Gly His Gly Pro Ala Glu Thr Gln Thr Leu
130 135 140

Gly Ser Leu Pro Asp Ile Asn Leu Thr Gln Ile Ser Thr Leu Ala Asn
145 150 155 160

Glu Leu Arg Asp Ser Arg Leu Ala Asn Asp Leu Arg Asp Ser Gly Ala
165 170 175

Thr Ile Arg Ile Gly
180

<210> SEQ ID NO 2
<211> LENGTH: 8
<212> TYPE: PRT
<213> ORGANISM: Artificial
<220> FEATURE:
<223> OTHER INFORMATION: Synthetic construct

<400> SEQUENCE: 2

Gly Tyr Thr Phe Thr Asp Tyr Thr
1 5

<210> SEQ ID NO 3
<211> LENGTH: 8

```
<212> TYPE: PRT
<213> ORGANISM: Artificial
<220> FEATURE:
<223> OTHER INFORMATION: Synthetic construct

<400> SEQUENCE: 3

Phe Tyr Pro Gly Ser His Ser Ile
1               5


<210> SEQ ID NO 4
<211> LENGTH: 9
<212> TYPE: PRT
<213> ORGANISM: Artificial
<220> FEATURE:
<223> OTHER INFORMATION: Synthetic construct

<400> SEQUENCE: 4

His Gly Gly Tyr Asp Gly Phe Asp Tyr
1               5


<210> SEQ ID NO 5
<211> LENGTH: 12
<212> TYPE: PRT
<213> ORGANISM: Artificial
<220> FEATURE:
<223> OTHER INFORMATION: Synthetic construct

<400> SEQUENCE: 5

Gln Ser Leu Phe Tyr Ser Thr Asn Gln Lys Asn Tyr
1               5                   10


<210> SEQ ID NO 6
<211> LENGTH: 4
<212> TYPE: PRT
<213> ORGANISM: Artificial
<220> FEATURE:
<223> OTHER INFORMATION: Synthetic construct

<400> SEQUENCE: 6

Trp Ala Ser Thr
1


<210> SEQ ID NO 7
<211> LENGTH: 9
<212> TYPE: PRT
<213> ORGANISM: Artificial
<220> FEATURE:
<223> OTHER INFORMATION: Synthetic construct

<400> SEQUENCE: 7

Gln Gln Tyr Tyr Tyr Phe Pro Tyr Thr
1               5


<210> SEQ ID NO 8
<211> LENGTH: 148
<212> TYPE: PRT
<213> ORGANISM: Artificial
<220> FEATURE:
<223> OTHER INFORMATION: Synthetic construct

<400> SEQUENCE: 8

Met Lys Cys Ser Trp Gly Ile Phe Phe Leu Leu Ser Val Thr Ala Gly
1               5                   10                  15

Val His Ser Lys Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
```

```
        35                  40                  45

Thr Asp Tyr Thr Ile His Trp Val Lys Gln Arg Ser Gly Gln Gly Leu
    50                  55                  60

Glu Trp Ile Gly Trp Phe Tyr Pro Gly Ser His Ser Ile Lys Tyr Asn
65                  70                  75                  80

Glu Gln Phe Lys Asp Arg Ala Thr Leu Thr Ala Asp Lys Ser Ser Ser
                85                  90                  95

Thr Val Tyr Met Glu Leu Ser Arg Leu Thr Ser Glu Asp Ser Ala Val
            100                 105                 110

Tyr Phe Cys Thr Arg His Gly Gly Tyr Asp Gly Phe Asp Tyr Trp Gly
        115                 120                 125

Gln Gly Thr Thr Leu Thr Val Ser Ser Ala Lys Thr Thr Pro Pro Ser
    130                 135                 140

Val Tyr Pro Leu
145


<210> SEQ ID NO 9
<211> LENGTH: 153
<212> TYPE: PRT
<213> ORGANISM: Artificial
<220> FEATURE:
<223> OTHER INFORMATION: Synthetic construct

<400> SEQUENCE: 9

Leu Asp Gly Gly Lys Met Asp Ser Gln Ala Gln Val Leu Met Leu Leu
1               5                   10                  15

Leu Leu Trp Val Ser Gly Thr Cys Gly Asp Ile Val Met Ser Gln Ser
            20                  25                  30

Pro Ser Ser Leu Ala Val Ser Val Gly Glu Lys Ile Thr Met Ser Cys
        35                  40                  45

Lys Ser Ser Gln Ser Leu Phe Tyr Ser Thr Asn Gln Lys Asn Tyr Leu
    50                  55                  60

Ala Trp Tyr Gln Gln Lys Pro Gly Gln Ser Pro Lys Leu Leu Ile Tyr
65                  70                  75                  80

Trp Ala Ser Thr Arg Glu Ser Gly Val Pro Asp Arg Phe Thr Gly Ser
                85                  90                  95

Gly Ser Gly Thr Asp Phe Thr Leu Thr Ile Ser Ser Val Lys Ala Glu
            100                 105                 110

Asp Leu Ala Val Tyr Tyr Cys Gln Gln Tyr Tyr Tyr Phe Pro Tyr Thr
        115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser
145                 150


<210> SEQ ID NO 10
<211> LENGTH: 316
<212> TYPE: PRT
<213> ORGANISM: Artificial
<220> FEATURE:
<223> OTHER INFORMATION: Synthetic construct

<400> SEQUENCE: 10

Met Lys Cys Ser Trp Gly Ile Phe Phe Leu Leu Ser Val Thr Ala Gly
1               5                   10                  15

Val His Ser Lys Val Gln Leu Gln Gln Ser Gly Ala Glu Leu Val Lys
            20                  25                  30
```

-continued

```
Pro Gly Ala Ser Val Lys Leu Ser Cys Lys Ala Ser Gly Tyr Thr Phe
        35                  40                  45

Thr Asp Tyr Thr Ile His Trp Val Lys Gln Arg Ser Gly Gln Gly Leu
    50                  55                  60

Glu Trp Ile Gly Trp Phe Tyr Pro Gly Ser His Ser Ile Lys Tyr Asn
65                  70                  75                  80

Glu Gln Phe Lys Asp Arg Ala Thr Leu Thr Ala Asp Lys Ser Ser Ser
                85                  90                  95

Thr Val Tyr Met Glu Leu Ser Arg Leu Thr Ser Glu Asp Ser Ala Val
            100                 105                 110

Tyr Phe Cys Thr Arg His Gly Gly Tyr Asp Gly Phe Asp Tyr Trp Gly
        115                 120                 125

Gln Gly Thr Thr Leu Thr Val Ser Ser Ala Lys Thr Thr Pro Pro Ser
    130                 135                 140

Val Tyr Pro Leu Gly Gly Gly Gly Ser Gly Gly Gly Gly Ser Gly Gly
145                 150                 155                 160

Gly Gly Ser Leu Asp Gly Gly Lys Met Asp Ser Gln Ala Gln Val Leu
                165                 170                 175

Met Leu Leu Leu Leu Trp Val Ser Gly Thr Cys Gly Asp Ile Val Met
            180                 185                 190

Ser Gln Ser Pro Ser Ser Leu Ala Val Ser Val Gly Glu Lys Ile Thr
        195                 200                 205

Met Ser Cys Lys Ser Ser Gln Ser Leu Phe Tyr Ser Thr Asn Gln Lys
    210                 215                 220

Asn Tyr Leu Ala Trp Tyr Gln Gln Lys Pro Gly Gln Ser Pro Lys Leu
225                 230                 235                 240

Leu Ile Tyr Trp Ala Ser Thr Arg Glu Ser Gly Val Pro Asp Arg Phe
                245                 250                 255

Thr Gly Ser Gly Ser Gly Thr Asp Phe Thr Leu Thr Ile Ser Ser Val
            260                 265                 270

Lys Ala Glu Asp Leu Ala Val Tyr Tyr Cys Gln Gln Tyr Tyr Tyr Phe
        275                 280                 285

Pro Tyr Thr Phe Gly Gly Gly Thr Lys Leu Glu Ile Lys Arg Ala Asp
    290                 295                 300

Ala Ala Pro Thr Val Ser Ile Phe Pro Pro Ser Ser
305                 310                 315


<210> SEQ ID NO 11
<211> LENGTH: 8
<212> TYPE: PRT
<213> ORGANISM: Artificial
<220> FEATURE:
<223> OTHER INFORMATION: Synthetic construct

<400> SEQUENCE: 11

Gly Tyr Thr Phe Thr Glu Tyr Thr
1               5


<210> SEQ ID NO 12
<211> LENGTH: 7
<212> TYPE: PRT
<213> ORGANISM: Artificial
<220> FEATURE:
<223> OTHER INFORMATION: Synthetic construct

<400> SEQUENCE: 12

Phe Tyr Pro Gly Ser Gly Ser
1               5
```

<210> SEQ ID NO 13
<211> LENGTH: 12
<212> TYPE: PRT
<213> ORGANISM: Artificial
<220> FEATURE:
<223> OTHER INFORMATION: Synthetic construct

<400> SEQUENCE: 13

```
Gln Ser Leu Leu Tyr Ser Asn Asn Gln Lys Asn Tyr
1               5                   10
```

<210> SEQ ID NO 14
<211> LENGTH: 9
<212> TYPE: PRT
<213> ORGANISM: Artificial
<220> FEATURE:
<223> OTHER INFORMATION: Synthetic construct

<400> SEQUENCE: 14

```
Gln Gln Tyr Tyr Ser Tyr Pro Phe Thr
1               5
```

<210> SEQ ID NO 15
<211> LENGTH: 175
<212> TYPE: PRT
<213> ORGANISM: Artificial
<220> FEATURE:
<223> OTHER INFORMATION: Synthetic construct

<400> SEQUENCE: 15

```
Met Gly Trp Ser Phe Ile Ile Leu Leu Ser Val Thr Ala Gly Val His
1               5                   10                  15

Ser Lys Val Gln Leu Gln Gln Ser Gly Ala Glu Leu Val Lys Pro Gly
            20                  25                  30

Ala Ser Val Lys Leu Ser Cys Lys Ala Ser Gly Tyr Thr Phe Thr Glu
        35                  40                  45

Tyr Thr Ile His Trp Val Lys Gln Arg Ser Gly Gln Gly Leu Glu Trp
    50                  55                  60

Ile Gly Trp Phe Tyr Pro Gly Ser Gly Ser Met Glu Tyr Asn Glu Lys
65                  70                  75                  80

Phe Asp Lys Ala Thr Leu Thr Ala Asp Asn Ser Ser Ser Thr Val Tyr
                85                  90                  95

Met Glu Leu Ser Arg Leu Thr Ser Glu Asp Ser Ala Val Tyr Phe Cys
            100                 105                 110

Glu Arg His Gly Gly Tyr Asp Gly Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ile Phe Leu Glu Asp Leu Leu Gln Tyr Ser Gln Leu Pro Trp Lys
145                 150                 155                 160

Ile Asp Val Leu Leu Leu Phe Ser Gln Asp Phe Gln Ala Val Tyr
                165                 170                 175
```

<210> SEQ ID NO 16
<211> LENGTH: 153
<212> TYPE: PRT
<213> ORGANISM: Artificial
<220> FEATURE:
<223> OTHER INFORMATION: Synthetic construct

<400> SEQUENCE: 16

```
Leu Asp Gly Gly Lys Met Asp Ser Gln Ala Gln Val Leu Met Leu Leu
1               5                   10                  15

Leu Leu Trp Val Ser Gly Thr Cys Gly Asp Ile Val Met Ser Gln Ser
            20                  25                  30

Pro Ser Ser Leu Ala Val Ser Val Gly Glu Lys Val Thr Met Ser Cys
        35                  40                  45

Lys Ser Ser Gln Ser Leu Leu Tyr Ser Asn Asn Gln Lys Asn Tyr Leu
    50                  55                  60

Ala Trp Tyr Gln Gln Lys Pro Gly Gln Ser Pro Lys Leu Leu Ile Tyr
65                  70                  75                  80

Trp Ala Ser Thr Arg Gly Ser Gly Val Pro Asp Arg Phe Thr Gly Ser
                85                  90                  95

Gly Ser Gly Thr Asp Phe Thr Leu Thr Ile Ser Ser Val Lys Ala Glu
            100                 105                 110

Asp Leu Ala Ile Tyr Tyr Cys Gln Gln Tyr Tyr Ser Tyr Pro Phe Thr
        115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser
145                 150


<210> SEQ ID NO 17
<211> LENGTH: 343
<212> TYPE: PRT
<213> ORGANISM: Artificial
<220> FEATURE:
<223> OTHER INFORMATION: Synthetic construct

<400> SEQUENCE: 17

Met Gly Trp Ser Phe Ile Ile Leu Leu Ser Val Thr Ala Gly Val His
1               5                   10                  15

Ser Lys Val Gln Leu Gln Gln Ser Gly Ala Glu Leu Val Lys Pro Gly
            20                  25                  30

Ala Ser Val Lys Leu Ser Cys Lys Ala Ser Gly Tyr Thr Phe Thr Glu
        35                  40                  45

Tyr Thr Ile His Trp Val Lys Gln Arg Ser Gly Gln Gly Leu Glu Trp
    50                  55                  60

Ile Gly Trp Phe Tyr Pro Gly Ser Gly Ser Met Glu Tyr Asn Glu Lys
65                  70                  75                  80

Phe Asp Lys Ala Thr Leu Thr Ala Asp Asn Ser Ser Ser Thr Val Tyr
                85                  90                  95

Met Glu Leu Ser Arg Leu Thr Ser Glu Asp Ser Ala Val Tyr Phe Cys
            100                 105                 110

Glu Arg His Gly Gly Tyr Asp Gly Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ile Phe Leu Glu Asp Leu Leu Gln Tyr Ser Gln Leu Pro Trp Lys
145                 150                 155                 160

Ile Asp Val Leu Leu Leu Phe Ser Gln Asp Phe Gln Ala Val Tyr Gly
                165                 170                 175

Gly Gly Gly Ser Gly Gly Gly Gly Ser Gly Gly Gly Gly Ser Leu Asp
            180                 185                 190

Gly Gly Lys Met Asp Ser Gln Ala Gln Val Leu Met Leu Leu Leu Leu
        195                 200                 205
```

```
Trp Val Ser Gly Thr Cys Gly Asp Ile Val Met Ser Gln Ser Pro Ser
    210                 215                 220

Ser Leu Ala Val Ser Val Gly Glu Lys Val Thr Met Ser Cys Lys Ser
225                 230                 235                 240

Ser Gln Ser Leu Leu Tyr Ser Asn Asn Gln Lys Asn Tyr Leu Ala Trp
                245                 250                 255

Tyr Gln Gln Lys Pro Gly Gln Ser Pro Lys Leu Leu Ile Tyr Trp Ala
            260                 265                 270

Ser Thr Arg Gly Ser Gly Val Pro Asp Arg Phe Thr Gly Ser Gly Ser
        275                 280                 285

Gly Thr Asp Phe Thr Leu Thr Ile Ser Ser Val Lys Ala Glu Asp Leu
    290                 295                 300

Ala Ile Tyr Tyr Cys Gln Gln Tyr Tyr Ser Tyr Pro Phe Thr Phe Gly
305                 310                 315                 320

Gly Gly Thr Lys Leu Glu Ile Lys Arg Ala Asp Ala Ala Pro Thr Val
                325                 330                 335

Ser Ile Phe Pro Pro Ser Ser
            340
```

<210> SEQ ID NO 18
<211> LENGTH: 543
<212> TYPE: DNA
<213> ORGANISM: Artificial
<220> FEATURE:
<223> OTHER INFORMATION: Synthetic construct

<400> SEQUENCE: 18

```
tccgaagtag aataccgggc tgaggtaggt caaaatgcgt acttgccatg cttctatacc     60

ccggcagcac cgggaaacct tgtgccagtg tgctggggta aaggagcttg ccccgttttt    120

gagtgtggca atgtagtgtt gcgcaccgat gaacgagatg ttaattattg gaccagccgg    180

tattggctta atggtgactt taggaaaggc gatgtctccc tcactatcga gaatgtgaca    240

ttggccgaca gcggaatcta ttgctgtcga attcaaatac ccggtatcat gaatgacgag    300

aagttcaatc ttaaattggt tatcaaacca gccaaggtga ctccggcacc cactaggcaa    360

cgagacttta cggcagcatt cccccggatg ctcacgactc gcggtcacgg acctgccgaa    420

acacagactc ttggttctct tcctgacatt aacctgaccc agatttccac acttgccaac    480

gagctccgcg actccagact cgctaatgac ctgcgcgatt caggagctac tataagaatc    540

ggt                                                                  543
```

<210> SEQ ID NO 19
<211> LENGTH: 15
<212> TYPE: PRT
<213> ORGANISM: Artificial
<220> FEATURE:
<223> OTHER INFORMATION: Synthetic construct

<400> SEQUENCE: 19

```
Gly Gly Gly Gly Ser Gly Gly Gly Gly Ser Gly Gly Gly Gly Ser
1               5                   10                  15
```

<210> SEQ ID NO 20
<211> LENGTH: 948
<212> TYPE: DNA
<213> ORGANISM: Artificial
<220> FEATURE:
<223> OTHER INFORMATION: Synthetic construct

<400> SEQUENCE: 20

```
atgaagtgta gctgggggat ctttttttctt ctcagtgtca ctgcaggagt gcattcaaaa     60
gtccaacttc agcaatcagg agcagaactg gtaaaaccgg gcgcctcagt taaactcagt    120
tgcaaagcta gtgggtacac cttcacagat tatacgattc actgggtaaa gcagaggagt    180
ggacaaggtt tggagtggat cggctggttt tatcccggaa gtcactcaat taaatacaac    240
gaacagttca aggatagagc tacgttgacc gctgacaaat cctcttcaac ggtatatatg    300
gagctttcaa ggcttacatc cgaagattca gcagtctatt tttgcaccag gcacggtggt    360
tacgacggat tcgattattg gggccaggga actactctga cagtgtcatc tgcgaaaaca    420
actccaccga gtgtttatcc tcttggcggc ggagggagtg gtggtggcgg atctgggga     480
ggtggatccc tcgacggcgg aaaaatggat tcacaggcgc aagtcttgat gttgttgttg    540
ctgtgggtat ccggcacctg tggcgacatc gtcatgtccc agtctccttc ctctcttgca    600
gtttcagtag gggaaaaaat aacaatgtcc tgtaaaagta gtcagtccct cttctacagt    660
acaaaccaga aaaactatct ggcatggtat cagcaaaaac cgggccagtc acccaaactg    720
ttgatctatt gggcttctac aagggagagc ggtgtgcccg acaggttcac tggctctggt    780
agtggcacag attttacgct gacgatatca tctgtcaagg ctgaggacct cgcggtctat    840
tactgtcagc aatactacta ttttccatat acttttggtg gtggaacaaa actggagatt    900
aagcgggctg atgcagcacc aacggttagt atatttccac cgtctagt                 948
```

<210> SEQ ID NO 21
<211> LENGTH: 1029
<212> TYPE: DNA
<213> ORGANISM: Artificial
<220> FEATURE:
<223> OTHER INFORMATION: Synthetic construct

<400> SEQUENCE: 21

```
atgggttggt catttattat tcttctctca gtaacagcgg gagtccactc caaggtacag     60
ctgcaacagt ctggcgcgga gctcgtaaaa ccaggggctt ctgtgaagtt gtcttgtaaa    120
gcgtcagggt atactttcac cgaatacacg atccactggg tgaagcagag gagcgggcaa    180
ggcctggagt ggatcggctg gttctacccc gggtcagggt ccatggagta caatgaaaaa    240
tttgataaag cgactctcac agccgacaat agttccagca cggtctatat ggaactttct    300
cggttgacat ccgaggactc agccgtatat ttttgtgagc gccacggagg atacgatggg    360
tttgattatt ggggacaggg gactacgctc acggtgagtt ccgctaagac tactccacct    420
agtgtgtacc cactgatctt cctcgaagac ctcttgcagt actcacaact tccgtggaaa    480
attgacgtgt tgcttttgtt tagccaggac tttcaagctg tctatggggg aggcggaagc    540
ggaggaggtg gtagtggagg cggggggtca ctggatgggg gtaaaatgga ttcacaagct    600
caggtactta tgctccttct gttgtgggtg tccgggactt gtggggacat cgtcatgtca    660
caaagcccat ctagtctggc cgtttcagta ggggaaaagg tgactatgtc ttgcaaaagc    720
agccaaagct tgctctatag taataaccaa aagaattacc tcgcatggta ccagcaaaag    780
ccagggcaat ctcctaaact gttgatctac tgggcttcaa ctcggggtag tggtgtgccc    840
gaccggttca cgggaagcgg gagcggaaca gatttcaccc tcacaatttc atctgtgaaa    900
gctgaggacc ttgccatcta ttactgtcaa cagtactact catatccctt cacgttcggc    960
ggtggcacaa agctcgaaat caagagagcg gacgctgcac ctactgtaag catttttcct   1020
ccctcttcc                                                           1029
```

<210> SEQ ID NO 22
<211> LENGTH: 69
<212> TYPE: DNA
<213> ORGANISM: Artificial
<220> FEATURE:
<223> OTHER INFORMATION: Synthetic construct

<400> SEQUENCE: 22
atgtacagga tgcaactcct gtcttgcatt gcactaagtc ttgcacttgt cacgaattcg 60
ggcgcgcct 69

<210> SEQ ID NO 23
<211> LENGTH: 759
<212> TYPE: DNA
<213> ORGANISM: Artificial
<220> FEATURE:
<223> OTHER INFORMATION: Synthetic construct

<400> SEQUENCE: 23
gctagcacca ctaccccggc ccctaggccc cctactccag cgccaactat agcatcacag 60
cctttgagct tgaggcccga agcttgcaga ccggcggcag ggggggctgt gcatacaagg 120
ggcctcgact ttgcctgcga catcgataat gagaagagca atggaaccat tatccatgtg 180
aaagggaaac acctttgtcc aagtccccta tttcccggac cttctaagcc cttttgggtg 240
ctggtggtgg ttggtggagt cctggcttgc tatagcttgc tagtaacagt ggcctttatt 300
attttctggg tgaggagtaa gaggagcagg ctcctgcaca gtgactacat gaacatgact 360
cccaggaggc ctgggccaac ccgcaagcat taccagccct atgccccacc acgcgacttc 420
gcagcctatc gctccagcag gagcgcagac gctcccgcgt accagcaggg ccagaaccag 480
ctctataacg agctcaatct aggacgaaga gaggagtacg atgttttgga caagagacgt 540
ggccgggacc ctgagatggg aggcaagccg agaaggaaga accctcagga aggcctgtac 600
aatgaactgc agaaagataa gatggcggag gcctacagtg agattgggat gaaaggcgag 660
cgccggaggg gcaaggggca cgatggcctt taccagggtc tcagtacagc caccaaggac 720
acctacgacg cccttcacat gcaggccctg cctcctcgc 759

<210> SEQ ID NO 24
<211> LENGTH: 23
<212> TYPE: PRT
<213> ORGANISM: Artificial
<220> FEATURE:
<223> OTHER INFORMATION: Synthetic construct

<400> SEQUENCE: 24

Met Tyr Arg Met Gln Leu Leu Ser Cys Ile Ala Leu Ser Leu Ala Leu
1 5 10 15

Val Thr Asn Ser Gly Ala Pro
20

<210> SEQ ID NO 25
<211> LENGTH: 253
<212> TYPE: PRT
<213> ORGANISM: Artificial
<220> FEATURE:
<223> OTHER INFORMATION: Synthetic construct

<400> SEQUENCE: 25

Ala Ser Thr Thr Thr Pro Ala Pro Arg Pro Pro Thr Pro Ala Pro Thr
1 5 10 15

```
Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Asp Asn Glu Lys Ser Asn Gly Thr Ile Ile His Val Lys Gly Lys His
    50                  55                  60

Leu Cys Pro Ser Pro Leu Phe Pro Gly Pro Ser Lys Pro Phe Trp Val
65                  70                  75                  80

Leu Val Val Val Gly Gly Val Leu Ala Cys Tyr Ser Leu Leu Val Thr
                85                  90                  95

Val Ala Phe Ile Ile Phe Trp Val Arg Ser Lys Arg Ser Arg Leu Leu
            100                 105                 110

His Ser Asp Tyr Met Asn Met Thr Pro Arg Arg Pro Gly Pro Thr Arg
        115                 120                 125

Lys His Tyr Gln Pro Tyr Ala Pro Pro Arg Asp Phe Ala Ala Tyr Arg
    130                 135                 140

Ser Ser Arg Ser Ala Asp Ala Pro Ala Tyr Gln Gln Gly Gln Asn Gln
145                 150                 155                 160

Leu Tyr Asn Glu Leu Asn Leu Gly Arg Arg Glu Glu Tyr Asp Val Leu
                165                 170                 175

Asp Lys Arg Arg Gly Arg Asp Pro Glu Met Gly Gly Lys Pro Arg Arg
            180                 185                 190

Lys Asn Pro Gln Glu Gly Leu Tyr Asn Glu Leu Gln Lys Asp Lys Met
        195                 200                 205

Ala Glu Ala Tyr Ser Glu Ile Gly Met Lys Gly Glu Arg Arg Arg Gly
    210                 215                 220

Lys Gly His Asp Gly Leu Tyr Gln Gly Leu Ser Thr Ala Thr Lys Asp
225                 230                 235                 240

Thr Tyr Asp Ala Leu His Met Gln Ala Leu Pro Pro Arg
                245                 250


<210> SEQ ID NO 26
<211> LENGTH: 144
<212> TYPE: PRT
<213> ORGANISM: Artificial
<220> FEATURE:
<223> OTHER INFORMATION: Synthetic construct

<400> SEQUENCE: 26

Thr Cys Arg Phe Ala Gly Val Phe His Val Glu Lys Asn Gly Arg Tyr
1               5                   10                  15

Ser Ile Ser Arg Thr Glu Ala Ala Asp Leu Cys Lys Ala Phe Asn Ser
            20                  25                  30

Thr Leu Pro Thr Met Ala Gln Met Glu Lys Ala Leu Ser Ile Gly Phe
        35                  40                  45

Glu Thr Cys Arg Tyr Gly Phe Ile Glu Gly His Val Val Ile Pro Arg
    50                  55                  60

Ile His Pro Asn Ser Ile Cys Ala Ala Asn Asn Thr Gly Val Tyr Ile
65                  70                  75                  80

Leu Thr Ser Asn Thr Ser Gln Tyr Asp Thr Tyr Cys Phe Asn Ala Ser
                85                  90                  95

Ala Pro Pro Glu Glu Asp Cys Thr Ser Val Thr Asp Leu Pro Asn Ala
            100                 105                 110

Phe Asp Gly Pro Ile Thr Ile Thr Ile Val Asn Arg Asp Gly Thr Arg
        115                 120                 125
```

```
Tyr Val Gln Lys Gly Glu Tyr Arg Thr Asn Pro Glu Asp Ile Tyr Pro
    130                 135                 140


<210> SEQ ID NO 27
<211> LENGTH: 173
<212> TYPE: PRT
<213> ORGANISM: Artificial
<220> FEATURE:
<223> OTHER INFORMATION: Synthetic construct

<400> SEQUENCE: 27

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170


<210> SEQ ID NO 28
<211> LENGTH: 182
<212> TYPE: PRT
<213> ORGANISM: Artificial
<220> FEATURE:
<223> OTHER INFORMATION: Synthetic construct

<400> SEQUENCE: 28

Thr Met Ala Ile Trp Arg Ser Asn Ser Gly Ser Asn Thr Leu Glu Asn
1               5                   10                  15

Gly Tyr Phe Leu Ser Arg Asn Lys Glu Asn His Ser Gln Pro Thr Gln
            20                  25                  30

Ser Ser Leu Glu Asp Ser Val Thr Pro Thr Lys Ala Val Lys Thr Thr
        35                  40                  45

Gly Val Leu Ser Ser Pro Cys Pro Pro Asn Trp Ile Ile Tyr Glu Lys
    50                  55                  60

Ser Cys Tyr Leu Phe Ser Met Ser Leu Asn Ser Trp Asp Gly Ser Lys
65                  70                  75                  80

Arg Gln Cys Trp Gln Leu Gly Ser Asn Leu Leu Lys Ile Asp Ser Ser
                85                  90                  95

Asn Glu Leu Gly Phe Ile Val Lys Gln Val Ser Ser Gln Pro Asp Asn
            100                 105                 110

Ser Phe Trp Ile Gly Leu Ser Arg Pro Gln Thr Glu Val Pro Trp Leu
```

115 120 125

Trp Glu Asp Gly Ser Thr Phe Ser Ser Asn Leu Phe Gln Ile Arg Thr
130 135 140

Thr Ala Thr Gln Glu Asn Pro Ser Pro Asn Cys Val Trp Ile His Val
145 150 155 160

Ser Val Ile Tyr Asp Gln Leu Cys Ser Val Pro Ser Tyr Ser Ile Cys
165 170 175

Glu Lys Lys Phe Ser Met
180

<210> SEQ ID NO 29
<211> LENGTH: 163
<212> TYPE: PRT
<213> ORGANISM: Artificial
<220> FEATURE:
<223> OTHER INFORMATION: Synthetic construct

<400> SEQUENCE: 29

Leu Gln Asp Pro Cys Ser Asn Cys Pro Ala Gly Thr Phe Cys Asp Asn
1 5 10 15

Asn Arg Asn Gln Ile Cys Ser Pro Cys Pro Pro Asn Ser Phe Ser Ser
20 25 30

Ala Gly Gly Gln Arg Thr Cys Asp Ile Cys Arg Gln Cys Lys Gly Val
35 40 45

Phe Arg Thr Arg Lys Glu Cys Ser Ser Thr Ser Asn Ala Glu Cys Asp
50 55 60

Cys Thr Pro Gly Phe His Cys Leu Gly Ala Gly Cys Ser Met Cys Glu
65 70 75 80

Gln Asp Cys Lys Gln Gly Gln Glu Leu Thr Lys Lys Gly Cys Lys Asp
85 90 95

Cys Cys Phe Gly Thr Phe Asn Asp Gln Lys Arg Gly Ile Cys Arg Pro
100 105 110

Trp Thr Asn Cys Ser Leu Asp Gly Lys Ser Val Leu Val Asn Gly Thr
115 120 125

Lys Glu Arg Asp Val Val Cys Gly Pro Ser Pro Ala Asp Leu Ser Pro
130 135 140

Gly Ala Ser Ser Val Thr Pro Pro Ala Pro Ala Arg Glu Pro Gly His
145 150 155 160

Ser Pro Gln

<210> SEQ ID NO 30
<211> LENGTH: 16
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(16)
<223> OTHER INFORMATION: x is any amino acid

<400> SEQUENCE: 30

Tyr Xaa Xaa Leu Xaa Xaa Xaa Xaa Xaa Xaa Xaa Xaa Tyr Xaa Xaa Leu
1 5 10 15